(12) United States Patent
Sotak et al.

(10) Patent No.: US 11,925,380 B2
(45) Date of Patent: *Mar. 12, 2024

(54) DISTAL END SUPPORTED TISSUE SLITTING APPARATUS

(71) Applicant: SPECTRANETICS LLC, Colorado Springs (CO)

(72) Inventors: Ryan Michael Sotak, Colorado Springs, CO (US); Michael Craig Anderson, Colorado Springs, CO (US); Kenneth P. Grace, Woodland Park, CO (US)

(73) Assignee: SPECTRANETICS LLC, Colorado Springs, CO (US)

( * ) Notice: Subject to any disclaimer, the term of this patent is extended or adjusted under 35 U.S.C. 154(b) by 649 days.

This patent is subject to a terminal disclaimer.

(21) Appl. No.: 16/950,196

(22) Filed: Nov. 17, 2020

(65) Prior Publication Data

US 2021/0068859 A1 Mar. 11, 2021

Related U.S. Application Data

(63) Continuation of application No. 14/192,445, filed on Feb. 27, 2014, now Pat. No. 10,835,279.

(Continued)

(51) Int. Cl.
*A61B 17/3205* (2006.01)
*A61B 17/32* (2006.01)
(Continued)

(52) U.S. Cl.
CPC .... *A61B 17/3205* (2013.01); *A61B 17/32053* (2013.01); *A61B 17/320725* (2013.01);
(Continued)

(58) Field of Classification Search
CPC .......... A61B 17/3205; A61B 17/32053; A61B 17/320725; A61B 17/320016; A61B 17/3207; A61B 17/3209; A61N 2001/0578
See application file for complete search history.

(56) References Cited

U.S. PATENT DOCUMENTS 1,663,761 A 3/1928 Johnson
3,400,708 A 9/1968 Scheidt
(Continued)

FOREIGN PATENT DOCUMENTS

DE 4038773 A1 6/1992
JP H05506382 A 9/1993
(Continued)

OTHER PUBLICATIONS

Extended European Search Report issued in EP Application No. 13836886.5, dated Apr. 7, 2016, 6 pages.
(Continued)

*Primary Examiner* — Sarah W Aleman
*Assistant Examiner* — Rachel S Highland

(57) ABSTRACT

Methods and systems for separating an object, such as a lead, from formed tissue are provided. Specifically, a tissue slitting apparatus is configured to engage formed tissue at a slitting engagement point. While the object is subjected to a first traction force, the tissue slitting apparatus is caused to move further into the engaged tissue and slit the tissue past the point of engagement. The slitting apparatus causes the tissue to separate along an axial direction of the length of the formed tissue and releases at least some of the force containing the object. The slitting apparatus is supported by a distal end support device configured to lock onto the lead. While supported, a slitting element of the apparatus places fibers of the formed tissue under tension and performs a lifting cut operation. The methods and systems are well
(Continued)

suited for use in cardiac pacing or defibrillator lead explant procedures.

13 Claims, 12 Drawing Sheets

Related U.S. Application Data

(60) Provisional application No. 61/784,203, filed on Mar. 14, 2013.

(51) Int. Cl.
*A61B 17/3207* (2006.01)
*A61B 17/3209* (2006.01)
*A61N 1/05* (2006.01)

(52) U.S. Cl.
CPC ... *A61B 17/320016* (2013.01); *A61B 17/3207* (2013.01); *A61B 17/3209* (2013.01); *A61N 2001/0578* (2013.01)

(56) References Cited

U.S. PATENT DOCUMENTS

| | | |
|---|---|---|
| 3,521,640 A | 7/1970 | Carey |
| 3,614,953 A | 10/1971 | Moss |
| 3,805,382 A | 4/1974 | Benedict |
| 3,831,274 A | 8/1974 | Horrocks |
| 3,858,577 A | 1/1975 | Bass et al. |
| 4,051,596 A | 10/1977 | Hofmann |
| 4,203,444 A | 5/1980 | Bonnell et al. |
| 4,246,902 A | 1/1981 | Martinez |
| 4,274,414 A | 6/1981 | Johnson et al. |
| 4,311,138 A | 1/1982 | Sugarman |
| 4,471,777 A | 9/1984 | McCorkle, Jr. |
| 4,517,977 A | 5/1985 | Frost |
| 4,559,927 A | 12/1985 | Chin |
| 4,566,438 A | 1/1986 | Liese et al. |
| 4,567,882 A | 2/1986 | Heller |
| 4,576,162 A | 3/1986 | McCorkle |
| 4,582,056 A | 4/1986 | McCorkle et al. |
| 4,598,710 A | 7/1986 | Kleinberg et al. |
| 4,627,436 A | 12/1986 | Leckrone |
| 4,641,912 A | 2/1987 | Goldenberg |
| 4,646,738 A | 3/1987 | Trott |
| 4,662,869 A | 5/1987 | Wright |
| 4,674,502 A | 6/1987 | Imonti |
| 4,718,417 A | 1/1988 | Kittrell |
| 4,729,763 A | 3/1988 | Henrie |
| 4,754,755 A | 7/1988 | Husted |
| 4,767,403 A | 8/1988 | Hodge |
| 4,844,062 A | 7/1989 | Wells |
| 4,862,886 A | 9/1989 | Clarke |
| 4,881,550 A * | 11/1989 | Kothe ............... A61B 10/02 600/564 |
| 4,911,148 A | 3/1990 | Sosnowski et al. |
| 4,943,289 A | 7/1990 | Goode et al. |
| 4,988,347 A | 1/1991 | Goode et al. |
| 4,997,424 A | 3/1991 | Little |
| 5,011,482 A | 4/1991 | Goode et al. |
| 5,013,310 A | 5/1991 | Goode et al. |
| 5,030,207 A | 7/1991 | Mersch et al. |
| 5,031,634 A | 7/1991 | Simon |
| 5,041,108 A | 8/1991 | Fox et al. |
| 5,114,403 A | 5/1992 | Clarke et al. |
| 5,139,494 A | 8/1992 | Freiberg |
| 5,139,495 A | 8/1992 | Daikuzono |
| 5,148,599 A | 9/1992 | Purcell |
| 5,152,744 A | 10/1992 | Krause et al. |
| 5,186,634 A | 2/1993 | Thompson |
| 5,201,316 A | 4/1993 | Pomeranz et al. |
| 5,207,683 A | 5/1993 | Goode et al. |
| 5,230,334 A | 7/1993 | Klopotek |
| 5,250,045 A | 10/1993 | Bohley |
| 5,263,928 A | 11/1993 | Trauthen et al. |
| 5,275,609 A | 1/1994 | Pingleton et al. |
| 5,290,275 A | 3/1994 | Kittrell et al. |
| 5,290,280 A | 3/1994 | Daikuzono |
| 5,290,303 A | 3/1994 | Pingleton et al. |
| 5,353,786 A | 10/1994 | Wilk |
| 5,358,487 A | 10/1994 | Miller |
| 5,373,840 A | 12/1994 | Knighton |
| 5,377,683 A | 1/1995 | Barken |
| 5,383,199 A | 1/1995 | Laudenslager et al. |
| 5,395,328 A | 3/1995 | Ockuly et al. |
| 5,396,902 A | 3/1995 | Brennen et al. |
| 5,423,330 A | 6/1995 | Lee |
| 5,423,806 A | 6/1995 | Dale et al. |
| 5,431,674 A | 7/1995 | Basile |
| 5,456,680 A | 10/1995 | Taylor et al. |
| 5,460,182 A | 10/1995 | Goodman et al. |
| 5,466,234 A | 11/1995 | Loeb et al. |
| 5,468,238 A | 11/1995 | Mersch |
| 5,470,330 A | 11/1995 | Goldenberg et al. |
| 5,484,433 A | 1/1996 | Taylor et al. |
| 5,507,751 A | 4/1996 | Goode et al. |
| 5,562,694 A | 10/1996 | Sauer et al. |
| 5,569,284 A | 10/1996 | Young et al. |
| 5,573,531 A | 11/1996 | Gregory |
| 5,575,797 A | 11/1996 | Neubauer et al. |
| 5,605,539 A | 2/1997 | Buelna et al. |
| 5,620,414 A | 4/1997 | Campbell et al. |
| 5,620,451 A | 4/1997 | Rosborough |
| 5,632,749 A | 5/1997 | Goode et al. |
| 5,651,781 A | 7/1997 | Grace |
| 5,665,051 A | 9/1997 | Quick |
| 5,667,473 A | 9/1997 | Finn et al. |
| 5,682,199 A | 10/1997 | Lankford |
| 5,697,936 A | 12/1997 | Sbipko et al. |
| 5,700,270 A | 12/1997 | Peyser |
| 5,707,389 A | 1/1998 | Louw et al. |
| 5,718,237 A | 2/1998 | Haaga |
| 5,725,523 A | 3/1998 | Mueller |
| 5,735,847 A | 4/1998 | Gough et al. |
| 5,746,738 A | 5/1998 | Cleary et al. |
| 5,766,164 A | 6/1998 | Mueller et al. |
| 5,782,823 A | 7/1998 | Mueller |
| 5,807,399 A | 9/1998 | Laske et al. |
| 5,814,044 A | 9/1998 | Hooven |
| 5,823,971 A | 10/1998 | Robinson et al. |
| 5,824,026 A | 10/1998 | Diaz |
| 5,825,958 A | 10/1998 | Gollihar |
| 5,863,294 A | 1/1999 | Alden |
| 5,873,886 A | 2/1999 | Larsen et al. |
| 5,879,365 A | 3/1999 | Whitfield et al. |
| 5,893,862 A | 4/1999 | Pratt et al. |
| 5,899,915 A | 5/1999 | Saadat |
| 5,906,611 A | 5/1999 | Dodick et al. |
| 5,910,150 A | 6/1999 | Saadat |
| 5,916,210 A | 6/1999 | Winston |
| 5,931,848 A | 8/1999 | Saadat |
| 5,941,893 A | 8/1999 | Saadat |
| 5,947,958 A | 9/1999 | Woodard et al. |
| 5,951,543 A | 9/1999 | Brauer |
| 5,951,581 A | 9/1999 | Saadat et al. |
| 5,970,982 A | 10/1999 | Perkins |
| 5,972,012 A | 10/1999 | Ream et al. |
| 5,980,515 A | 11/1999 | Tu |
| 5,980,545 A | 11/1999 | Pacala et al. |
| 5,989,243 A | 11/1999 | Goldenberg |
| 6,007,512 A | 12/1999 | Hooven |
| 6,010,476 A | 1/2000 | Saadat |
| 6,019,756 A | 2/2000 | Mueller et al. |
| 6,022,336 A | 2/2000 | Zadno-Azizi et al. |
| 6,027,450 A | 2/2000 | Brown et al. |
| 6,027,497 A | 2/2000 | Daniel et al. |
| 6,033,402 A | 3/2000 | Tu et al. |
| 6,036,685 A | 3/2000 | Mueller |
| 6,051,008 A | 4/2000 | Saadat et al. |
| 6,066,131 A | 5/2000 | Mueller et al. |
| 6,080,175 A | 6/2000 | Hogendijk |
| 6,083,237 A | 7/2000 | Huitema et al. |
| 6,099,537 A | 8/2000 | Sugai et al. |

(56) References Cited

U.S. PATENT DOCUMENTS

| | | |
|---|---|---|
| 6,102,926 A | 8/2000 | Tartaglia et al. |
| 6,117,128 A | 9/2000 | Gregory |
| 6,120,520 A | 9/2000 | Saadat et al. |
| 6,123,718 A | 9/2000 | Tu |
| 6,126,654 A | 10/2000 | Giba et al. |
| 6,129,897 A | 10/2000 | Daikuzono |
| 6,136,005 A | 10/2000 | Goode et al. |
| 6,139,543 A | 10/2000 | Esch et al. |
| 6,152,909 A | 11/2000 | Bagaoisan et al. |
| 6,152,918 A | 11/2000 | Padilla et al. |
| 6,156,049 A | 12/2000 | Lovato et al. |
| 6,159,203 A | 12/2000 | Sinofsky |
| 6,159,225 A | 12/2000 | Makower |
| 6,162,214 A | 12/2000 | Mueller et al. |
| 6,165,188 A | 12/2000 | Saadat et al. |
| 6,167,315 A | 12/2000 | Coe et al. |
| 6,174,307 B1 | 1/2001 | Daniel et al. |
| 6,190,352 B1 | 2/2001 | Haarala et al. |
| 6,190,353 B1 | 2/2001 | Makower et al. |
| 6,193,650 B1 | 2/2001 | Ryan et al. |
| 6,203,537 B1 | 3/2001 | Adrian |
| 6,210,400 B1 | 4/2001 | Hebert et al. |
| 6,228,052 B1 | 5/2001 | Pohndorf |
| 6,228,076 B1 | 5/2001 | Winston et al. |
| 6,235,044 B1 | 5/2001 | Root et al. |
| 6,241,692 B1 | 6/2001 | Tu et al. |
| 6,245,011 B1 | 6/2001 | Dudda et al. |
| 6,251,121 B1 | 6/2001 | Saadat |
| 6,258,083 B1 | 7/2001 | Daniel et al. |
| 6,290,668 B1 | 9/2001 | Gregory et al. |
| 6,315,774 B1 | 11/2001 | Daniel et al. |
| 6,324,434 B2 | 11/2001 | Coe et al. |
| 6,368,318 B1 | 4/2002 | Visuri et al. |
| 6,395,002 B1 | 5/2002 | Ellman et al. |
| 6,398,773 B1 | 6/2002 | Bagaoisan et al. |
| 6,402,771 B1 | 6/2002 | Palmer et al. |
| 6,402,781 B1 | 6/2002 | Langberg et al. |
| 6,419,674 B1 | 7/2002 | Bowser et al. |
| 6,419,684 B1 | 7/2002 | Heisler et al. |
| 6,423,051 B1 | 7/2002 | Kaplan et al. |
| 6,428,539 B1 | 8/2002 | Baxter et al. |
| 6,428,556 B1 | 8/2002 | Chin |
| 6,432,119 B1 | 8/2002 | Saadat |
| 6,436,054 B1 | 8/2002 | Viola et al. |
| 6,436,114 B1 | 8/2002 | Novak et al. |
| 6,440,125 B1 | 8/2002 | Rentrop |
| 6,454,741 B1 | 9/2002 | Muni et al. |
| 6,454,758 B1 | 9/2002 | Thompson et al. |
| 6,461,349 B1 | 10/2002 | Elbrecht et al. |
| 6,478,777 B1 | 11/2002 | Honeck et al. |
| 6,485,413 B1 | 11/2002 | Boppart et al. |
| 6,485,485 B1 | 11/2002 | Winston et al. |
| 6,488,636 B2 | 12/2002 | Bryan et al. |
| 6,500,182 B2 | 12/2002 | Foster |
| 6,512,959 B1 | 1/2003 | Gomperz et al. |
| 6,527,752 B1 | 3/2003 | Bosley et al. |
| 6,537,314 B2 | 3/2003 | Langberg et al. |
| 6,554,779 B2 | 4/2003 | Viola et al. |
| 6,558,382 B2 | 5/2003 | Jahns et al. |
| 6,565,583 B1 | 5/2003 | Deaton et al. |
| 6,565,588 B1 | 5/2003 | Clement et al. |
| 6,569,082 B1 | 5/2003 | Chin |
| 6,575,997 B1 | 6/2003 | Palmer et al. |
| 6,592,607 B1 | 7/2003 | Palmer et al. |
| 6,595,982 B2 | 7/2003 | Sekino et al. |
| 6,599,296 B1 | 7/2003 | Gillick et al. |
| 6,602,241 B2 | 8/2003 | Makower et al. |
| 6,607,547 B1 | 8/2003 | Chin |
| 6,610,046 B1 | 8/2003 | Usami et al. |
| 6,610,066 B2 | 8/2003 | Dinger et al. |
| 6,613,013 B2 | 9/2003 | Haarala et al. |
| 6,620,153 B2 | 9/2003 | Mueller et al. |
| 6,620,160 B2 | 9/2003 | Lewis et al. |
| 6,620,180 B2 | 9/2003 | Bays et al. |
| 6,641,590 B1 | 11/2003 | Palmer et al. |
| 6,652,480 B1 | 11/2003 | Imran et al. |
| 6,652,548 B2 | 11/2003 | Evans et al. |
| 6,660,021 B1 | 12/2003 | Palmer et al. |
| 6,663,621 B1 | 12/2003 | Winston |
| 6,663,626 B2 | 12/2003 | Truckai et al. |
| 6,669,685 B1 | 12/2003 | Rizoiu et al. |
| 6,673,090 B2 | 1/2004 | Root et al. |
| 6,687,548 B2 | 2/2004 | Goode |
| 6,702,813 B1 | 3/2004 | Baxter et al. |
| 6,706,018 B2 | 3/2004 | Westlund et al. |
| 6,706,052 B1 | 3/2004 | Chin |
| 6,706,065 B2 | 3/2004 | Langberg et al. |
| 6,709,456 B2 | 3/2004 | Langberg et al. |
| 6,712,773 B1 | 3/2004 | Viola |
| 6,712,826 B2 | 3/2004 | Lui |
| 6,772,014 B2 | 8/2004 | Coe et al. |
| 6,802,838 B2 | 10/2004 | Loeb et al. |
| 6,805,692 B2 | 10/2004 | Muni et al. |
| 6,810,882 B2 | 11/2004 | Langberg et al. |
| 6,818,001 B2 | 11/2004 | Wulfman et al. |
| 6,855,143 B2 | 2/2005 | Davison |
| 6,858,027 B2 | 2/2005 | Redtenbacher et al. |
| 6,860,860 B2 | 3/2005 | Viola |
| 6,869,431 B2 | 3/2005 | Maguire et al. |
| 6,871,085 B2 | 3/2005 | Sommer |
| 6,884,240 B1 | 4/2005 | Dykes |
| 6,887,238 B2 | 5/2005 | Jahns et al. |
| 6,893,450 B2 | 5/2005 | Foster |
| 6,913,612 B2 | 7/2005 | Palmer et al. |
| 6,962,585 B2 | 11/2005 | Poleo et al. |
| 6,966,906 B2 | 11/2005 | Brown |
| 6,979,290 B2 | 12/2005 | Mourlas et al. |
| 6,979,319 B2 | 12/2005 | Manning et al. |
| 6,989,028 B2 | 1/2006 | Lashinski et al. |
| 6,999,809 B2 | 2/2006 | Currier et al. |
| 7,004,956 B2 | 2/2006 | Palmer et al. |
| 7,011,682 B2 | 3/2006 | Lashinski et al. |
| 7,029,467 B2 | 4/2006 | Currier et al. |
| 7,033,335 B2 | 4/2006 | Haarala et al. |
| 7,033,344 B2 | 4/2006 | Imran |
| 7,033,357 B2 | 4/2006 | Baxter et al. |
| 7,060,061 B2 | 6/2006 | Altshuler et al. |
| 7,063,693 B2 | 6/2006 | Guenst |
| 7,077,856 B2 | 7/2006 | Whitman |
| 7,092,765 B2 | 8/2006 | Geske et al. |
| 7,104,983 B2 | 9/2006 | Grasso et al. |
| 7,114,642 B2 | 10/2006 | Whitman |
| 7,117,039 B2 | 10/2006 | Manning et al. |
| 7,149,587 B2 | 12/2006 | Wardle et al. |
| 7,151,965 B2 | 12/2006 | Osypka |
| 7,189,207 B2 | 3/2007 | Viola |
| 7,191,015 B2 | 3/2007 | Lamson et al. |
| 7,192,430 B2 | 3/2007 | Truckai et al. |
| 7,204,824 B2 | 4/2007 | Moulis |
| 7,214,180 B2 | 5/2007 | Chin |
| 7,226,459 B2 | 6/2007 | Cesarini et al. |
| 7,238,179 B2 | 7/2007 | Brucker et al. |
| 7,238,180 B2 | 7/2007 | Mester et al. |
| 7,252,641 B2 | 8/2007 | Thompson et al. |
| 7,264,587 B2 | 9/2007 | Chin |
| 7,273,478 B2 | 9/2007 | Appling et al. |
| 7,276,052 B2 | 10/2007 | Kobayashi et al. |
| 7,288,096 B2 | 10/2007 | Chin |
| 7,296,577 B2 | 11/2007 | Lashinski et al. |
| 7,306,588 B2 | 12/2007 | Loeb et al. |
| 7,326,226 B2 | 2/2008 | Root et al. |
| 7,328,071 B1 | 2/2008 | Stehr et al. |
| 7,344,546 B2 | 3/2008 | Wulfman et al. |
| 7,357,794 B2 | 4/2008 | Makower et al. |
| 7,359,756 B2 | 4/2008 | Goode |
| 7,369,901 B1 | 5/2008 | Morgan et al. |
| 7,392,095 B2 | 6/2008 | Flynn et al. |
| 7,396,354 B2 | 7/2008 | Rychnovsky et al. |
| 7,398,781 B1 | 7/2008 | Chin |
| 7,449,010 B1 | 11/2008 | Hayase et al. |
| 7,462,167 B2 | 12/2008 | Kratz et al. |
| 7,485,127 B2 | 2/2009 | Nistal |
| 7,494,484 B2 | 2/2009 | Beck et al. |
| 7,507,252 B2 | 3/2009 | Lashinski et al. |

(56) References Cited

U.S. PATENT DOCUMENTS

| | | |
|---|---|---|
| 7,509,169 B2 | 3/2009 | Eigler et al. |
| 7,510,524 B2 | 3/2009 | Vayser et al. |
| 7,510,576 B2 | 3/2009 | Langberg et al. |
| 7,513,877 B2 | 4/2009 | Viola |
| 7,513,892 B1 | 4/2009 | Haarala et al. |
| 7,526,342 B2 | 4/2009 | Chin et al. |
| 7,537,602 B2 | 5/2009 | Whitman |
| 7,540,865 B2 | 6/2009 | Griffin et al. |
| 7,544,197 B2 | 6/2009 | Kelsch et al. |
| 7,559,941 B2 | 7/2009 | Zannis et al. |
| D600,792 S | 9/2009 | Eubanks et al. |
| 7,591,790 B2 | 9/2009 | Pflueger |
| 7,597,698 B2 | 10/2009 | Chin |
| 7,606,615 B2 | 10/2009 | Makower et al. |
| 7,611,474 B2 | 11/2009 | Hibner et al. |
| 7,637,904 B2 | 12/2009 | Wingler et al. |
| 7,645,286 B2 | 1/2010 | Catanese et al. |
| 7,648,466 B2 | 1/2010 | Stephens et al. |
| 7,651,503 B1 | 1/2010 | Coe et al. |
| 7,651,504 B2 | 1/2010 | Goode et al. |
| D610,259 S | 2/2010 | Way et al. |
| D611,146 S | 3/2010 | Way et al. |
| 7,674,272 B2 | 3/2010 | Torrance et al. |
| 7,695,485 B2 | 4/2010 | Whitman et al. |
| 7,695,512 B2 | 4/2010 | Lashinski et al. |
| 7,697,996 B2 | 4/2010 | Manning et al. |
| 7,713,231 B2 | 5/2010 | Wulfman et al. |
| 7,713,235 B2 | 5/2010 | Torrance et al. |
| 7,713,281 B2 | 5/2010 | Leeflang et al. |
| 7,722,549 B2 | 5/2010 | Nakao |
| 7,740,626 B2 | 6/2010 | Takayama et al. |
| 7,743,960 B2 | 6/2010 | Whitman et al. |
| D619,252 S | 7/2010 | Way et al. |
| D619,253 S | 7/2010 | Way et al. |
| 7,758,594 B2 | 7/2010 | Lamson et al. |
| 7,758,613 B2 | 7/2010 | Whitman |
| D621,939 S | 8/2010 | Way et al. |
| 7,766,923 B2 | 8/2010 | Catanese et al. |
| 7,780,682 B2 | 8/2010 | Catanese et al. |
| 7,780,694 B2 | 8/2010 | Palmer et al. |
| 7,794,411 B2 | 9/2010 | Ritchart et al. |
| 7,798,813 B1 | 9/2010 | Harrel |
| 7,801,624 B1 | 9/2010 | Flannery et al. |
| 7,803,151 B2 | 9/2010 | Whitman |
| 7,806,835 B2 | 10/2010 | Hibner et al. |
| 7,811,281 B1 | 10/2010 | Rentrop |
| 7,815,655 B2 | 10/2010 | Catanese et al. |
| 7,842,009 B2 | 11/2010 | Torrance et al. |
| 7,845,538 B2 | 12/2010 | Whitman |
| 7,858,038 B2 | 12/2010 | Andreyko et al. |
| 7,875,018 B2 | 1/2011 | Tockman et al. |
| 7,875,049 B2 | 1/2011 | Eversull et al. |
| 7,890,186 B2 | 2/2011 | Wardle et al. |
| 7,890,192 B1 | 2/2011 | Kelsch et al. |
| 7,896,879 B2 | 3/2011 | Solsberg et al. |
| 7,896,891 B2 | 3/2011 | Catanese et al. |
| 7,905,889 B2 | 3/2011 | Catanese et al. |
| 7,909,836 B2 | 3/2011 | McLean et al. |
| 7,914,464 B2 | 3/2011 | Burdorff et al. |
| 7,914,542 B2 | 3/2011 | Lamson et al. |
| D635,671 S | 4/2011 | Way et al. |
| 7,918,230 B2 | 4/2011 | Whitman et al. |
| 7,918,803 B2 | 4/2011 | Ritchart et al. |
| 7,930,040 B1 | 4/2011 | Kelsch et al. |
| 7,935,146 B2 | 5/2011 | Langberg et al. |
| 7,938,786 B2 | 5/2011 | Ritchie et al. |
| 7,942,830 B2 | 5/2011 | Solsberg et al. |
| 7,951,071 B2 | 5/2011 | Whitman et al. |
| 7,951,158 B2 | 5/2011 | Catanese et al. |
| 7,963,040 B2 | 6/2011 | Shan et al. |
| 7,963,433 B2 | 6/2011 | Whitman et al. |
| 7,974,710 B2 | 7/2011 | Seifert |
| 7,981,049 B2 | 7/2011 | Ritchie et al. |
| 7,981,050 B2 | 7/2011 | Ritchart et al. |
| 7,981,128 B2 | 7/2011 | To et al. |
| 7,988,726 B2 | 8/2011 | Langberg et al. |
| 7,991,258 B2 | 8/2011 | Temelkuran et al. |
| 7,992,758 B2 | 8/2011 | Whitman et al. |
| 7,993,350 B2 | 8/2011 | Ventura et al. |
| 7,993,351 B2 | 8/2011 | Worley et al. |
| 7,993,359 B1 | 8/2011 | Atwell et al. |
| 8,007,469 B2 | 8/2011 | Duffy |
| 8,007,488 B2 | 8/2011 | Ravenscroft |
| 8,007,503 B2 | 8/2011 | Catanese et al. |
| 8,007,506 B2 | 8/2011 | To et al. |
| 8,016,748 B2 | 9/2011 | Mourlas et al. |
| 8,016,844 B2 | 9/2011 | Privitera et al. |
| 8,016,855 B2 | 9/2011 | Whitman et al. |
| 8,016,858 B2 | 9/2011 | Whitman |
| 8,021,373 B2 | 9/2011 | Whitman et al. |
| 8,025,199 B2 | 9/2011 | Whitman et al. |
| 8,043,309 B2 | 10/2011 | Catanese et al. |
| RE42,959 E | 11/2011 | Saadat et al. |
| 8,052,616 B2 | 11/2011 | Andrisek et al. |
| 8,052,659 B2 | 11/2011 | Ravenscroft et al. |
| 8,056,786 B2 | 11/2011 | Whitman et al. |
| 8,056,791 B2 | 11/2011 | Whitman |
| 8,070,762 B2 | 12/2011 | Escudero et al. |
| 8,090,430 B2 | 1/2012 | Makower et al. |
| 8,097,012 B2 | 1/2012 | Kagarise |
| 8,100,920 B2 | 1/2012 | Gambale et al. |
| 8,118,208 B2 | 2/2012 | Whitman |
| 8,126,570 B2 | 2/2012 | Manning et al. |
| 8,128,577 B2 | 3/2012 | Viola |
| 8,128,636 B2 | 3/2012 | Lui et al. |
| 8,133,214 B2 | 3/2012 | Hayase et al. |
| 8,137,377 B2 | 3/2012 | Palmer et al. |
| 8,142,442 B2 | 3/2012 | Palmer et al. |
| 8,142,446 B2 | 3/2012 | Shan |
| RE43,300 E | 4/2012 | Saadat et al. |
| 8,157,815 B2 | 4/2012 | Catanese et al. |
| 8,186,559 B1 | 5/2012 | Whitman |
| 8,187,204 B2 | 5/2012 | Miller et al. |
| 8,187,268 B2 | 5/2012 | Godara et al. |
| 8,192,430 B2 | 6/2012 | Goode et al. |
| 8,202,229 B2 | 6/2012 | Miller et al. |
| 8,206,409 B2 | 6/2012 | Privitera et al. |
| 8,211,118 B2 | 7/2012 | Catanese et al. |
| 8,216,254 B2 | 7/2012 | McLean et al. |
| 8,235,916 B2 | 8/2012 | Whiting et al. |
| 8,236,016 B2 | 8/2012 | To et al. |
| 8,239,039 B2 | 8/2012 | Zarembo et al. |
| 8,241,272 B2 | 8/2012 | Arnold et al. |
| 8,251,916 B2 | 8/2012 | Speeg et al. |
| 8,252,015 B2 | 8/2012 | Leeflang et al. |
| 8,257,312 B2 | 9/2012 | Duffy |
| 8,272,554 B2 | 9/2012 | Whitman et al. |
| 8,273,078 B2 | 9/2012 | Muenker |
| 8,295,947 B2 | 10/2012 | Lamson et al. |
| 8,303,511 B2 | 11/2012 | Eigler et al. |
| 8,323,240 B2 | 12/2012 | Wulfman et al. |
| 8,326,437 B2 | 12/2012 | Cully et al. |
| 8,333,740 B2 | 12/2012 | Shippert |
| 8,333,776 B2 | 12/2012 | Cheng et al. |
| 8,337,516 B2 | 12/2012 | Escudero et al. |
| 8,343,167 B2 | 1/2013 | Henson |
| 8,343,187 B2 | 1/2013 | Lamson et al. |
| 8,353,899 B1 | 1/2013 | Wells et al. |
| 8,361,094 B2 | 1/2013 | To et al. |
| 8,364,280 B2 | 1/2013 | Marnfeldt et al. |
| 8,372,098 B2 | 2/2013 | Tran |
| 8,394,110 B2 | 3/2013 | Catanese et al. |
| 8,394,113 B2 | 3/2013 | Wei et al. |
| 8,425,535 B2 | 4/2013 | McLean et al. |
| 8,632,558 B2 | 1/2014 | Chin et al. |
| 2001/0005789 A1 | 6/2001 | Root et al. |
| 2001/0016717 A1 | 8/2001 | Haarala et al. |
| 2001/0025174 A1 | 9/2001 | Daniel et al. |
| 2001/0031981 A1 | 10/2001 | Evans et al. |
| 2001/0041899 A1 | 11/2001 | Foster |
| 2002/0002372 A1 | 1/2002 | Jahns et al. |
| 2002/0007204 A1 | 1/2002 | Goode |
| 2002/0010475 A1 | 1/2002 | Lui |
| 2002/0010487 A1 | 1/2002 | Evans et al. |

(56) References Cited

U.S. PATENT DOCUMENTS

| | | |
|---|---|---|
| 2002/0016628 A1 | 2/2002 | Langberg et al. |
| 2002/0026127 A1 | 2/2002 | Balbierz |
| 2002/0042610 A1 | 4/2002 | Sliwa et al. |
| 2002/0045811 A1 | 4/2002 | Kittrell et al. |
| 2002/0065543 A1 | 5/2002 | Gomperz et al. |
| 2002/0068954 A1 | 6/2002 | Foster |
| 2002/0077593 A1 | 6/2002 | Perkins et al. |
| 2002/0087151 A1 | 7/2002 | Mody et al. |
| 2002/0103477 A1 | 8/2002 | Grasso et al. |
| 2002/0103532 A1 | 8/2002 | Langberg et al. |
| 2002/0103533 A1 | 8/2002 | Langberg et al. |
| 2002/0123785 A1 | 9/2002 | Zhang et al. |
| 2002/0151961 A1 | 10/2002 | Lashinski et al. |
| 2002/0156346 A1 | 10/2002 | Kamrava et al. |
| 2002/0183735 A1 | 12/2002 | Edwards et al. |
| 2002/0188278 A1 | 12/2002 | Tockman et al. |
| 2003/0009146 A1 | 1/2003 | Muni et al. |
| 2003/0009157 A1 | 1/2003 | Levine et al. |
| 2003/0050630 A1 | 3/2003 | Mody et al. |
| 2003/0050631 A1 | 3/2003 | Mody et al. |
| 2003/0055444 A1 | 3/2003 | Evans et al. |
| 2003/0055445 A1 | 3/2003 | Evans et al. |
| 2003/0065312 A1 | 4/2003 | Owa |
| 2003/0065316 A1 | 4/2003 | Levine et al. |
| 2003/0069575 A1 | 4/2003 | Chin et al. |
| 2003/0073985 A1 | 4/2003 | Mueller et al. |
| 2003/0078562 A1 | 4/2003 | Makower et al. |
| 2003/0092995 A1 | 5/2003 | Thompson |
| 2003/0105451 A1 | 6/2003 | Westlund et al. |
| 2003/0125619 A1 | 7/2003 | Manning et al. |
| 2003/0144594 A1 | 7/2003 | Gellman |
| 2003/0167056 A1 | 9/2003 | Jahns et al. |
| 2003/0181935 A1 | 9/2003 | Gardeski et al. |
| 2003/0187460 A1 | 10/2003 | Chin et al. |
| 2003/0187461 A1 | 10/2003 | Chin |
| 2003/0199921 A1 | 10/2003 | Palmer et al. |
| 2003/0204202 A1 | 10/2003 | Palmer et al. |
| 2003/0208209 A1 | 11/2003 | Gambale et al. |
| 2003/0229323 A1 | 12/2003 | Haarala et al. |
| 2003/0229353 A1 | 12/2003 | Cragg |
| 2004/0006358 A1 | 1/2004 | Wulfman et al. |
| 2004/0010248 A1 | 1/2004 | Appling et al. |
| 2004/0015193 A1 | 1/2004 | Lamson et al. |
| 2004/0019359 A1 | 1/2004 | Worley et al. |
| 2004/0049208 A1 | 3/2004 | Hill et al. |
| 2004/0054368 A1 | 3/2004 | Truckai et al. |
| 2004/0054388 A1 | 3/2004 | Osypka |
| 2004/0059348 A1 | 3/2004 | Geske et al. |
| 2004/0059404 A1 | 3/2004 | Bjorklund |
| 2004/0064024 A1 | 4/2004 | Sommer |
| 2004/0068256 A1 | 4/2004 | Rizoiu et al. |
| 2004/0068288 A1 | 4/2004 | Palmer et al. |
| 2004/0093016 A1 | 5/2004 | Root et al. |
| 2004/0097788 A1 | 5/2004 | Mourlas et al. |
| 2004/0102804 A1 | 5/2004 | Chin |
| 2004/0102841 A1 | 5/2004 | Langberg et al. |
| 2004/0111101 A1 | 6/2004 | Chin |
| 2004/0116939 A1 | 6/2004 | Goode |
| 2004/0116992 A1 | 6/2004 | Wardle et al. |
| 2004/0133220 A1 | 7/2004 | Lashinski et al. |
| 2004/0138528 A1 | 7/2004 | Richter et al. |
| 2004/0138562 A1 | 7/2004 | Makower et al. |
| 2004/0138744 A1 | 7/2004 | Lashinski et al. |
| 2004/0143284 A1 | 7/2004 | Chin |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0153096 A1 | 8/2004 | Goode et al. |
| 2004/0153098 A1 | 8/2004 | Chin et al. |
| 2004/0153146 A1 | 8/2004 | Lashinski et al. |
| 2004/0158236 A1 | 8/2004 | Thyzel |
| 2004/0172116 A1 | 9/2004 | Seifert et al. |
| 2004/0176840 A1 | 9/2004 | Langberg et al. |
| 2004/0181249 A1 | 9/2004 | Torrance et al. |
| 2004/0216748 A1 | 11/2004 | Chin |
| 2004/0220519 A1 | 11/2004 | Wulfman et al. |
| 2004/0225280 A1 | 11/2004 | Horrigan |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0236397 A1 | 11/2004 | Coe et al. |
| 2004/0243123 A1 | 12/2004 | Grasso et al. |
| 2004/0243162 A1 | 12/2004 | Wulfman et al. |
| 2004/0254534 A1 | 12/2004 | Bjorkman et al. |
| 2004/0260322 A1 | 12/2004 | Rudko et al. |
| 2004/0267276 A1 | 12/2004 | Camino et al. |
| 2004/0267304 A1 | 12/2004 | Zannis et al. |
| 2005/0004644 A1 | 1/2005 | Kelsch et al. |
| 2005/0025798 A1 | 2/2005 | Moulis |
| 2005/0027199 A1 | 2/2005 | Clarke |
| 2005/0027337 A1 | 2/2005 | Rudko et al. |
| 2005/0038419 A9 | 2/2005 | Arnold et al. |
| 2005/0060030 A1 | 3/2005 | Lashinski et al. |
| 2005/0065561 A1 | 3/2005 | Manning et al. |
| 2005/0090748 A1 | 4/2005 | Makower et al. |
| 2005/0096643 A1 | 5/2005 | Brucker |
| 2005/0096740 A1 | 5/2005 | Langberg et al. |
| 2005/0131399 A1 | 6/2005 | Loeb et al. |
| 2005/0149104 A1 | 7/2005 | Leeflang et al. |
| 2005/0149105 A1 | 7/2005 | Leeflang et al. |
| 2005/0165288 A1 | 7/2005 | Rioux et al. |
| 2005/0197623 A1 | 9/2005 | Leeflang et al. |
| 2005/0222607 A1 | 10/2005 | Palmer et al. |
| 2005/0228402 A1 | 10/2005 | Hofmann |
| 2005/0228452 A1 | 10/2005 | Mourlas et al. |
| 2005/0251116 A1 | 11/2005 | Steinke et al. |
| 2005/0259942 A1 | 11/2005 | Temelkuran et al. |
| 2005/0273090 A1 | 12/2005 | Nieman et al. |
| 2005/0283143 A1 | 12/2005 | Rizoiu |
| 2005/0288596 A1 | 12/2005 | Eigler et al. |
| 2005/0288604 A1 | 12/2005 | Eigler et al. |
| 2005/0288654 A1 | 12/2005 | Nieman et al. |
| 2005/0288722 A1 | 12/2005 | Eigler et al. |
| 2006/0004317 A1 | 1/2006 | Mauge et al. |
| 2006/0052660 A1 | 3/2006 | Chin |
| 2006/0084839 A1 | 4/2006 | Mourlas et al. |
| 2006/0100663 A1 | 5/2006 | Palmer et al. |
| 2006/0116746 A1 | 6/2006 | Chin |
| 2006/0116757 A1 | 6/2006 | Lashinski et al. |
| 2006/0167417 A1 | 7/2006 | Kratz et al. |
| 2006/0173440 A1 | 8/2006 | Lamson et al. |
| 2006/0217755 A1 | 9/2006 | Eversull et al. |
| 2006/0229490 A1 | 10/2006 | Chin |
| 2006/0235431 A1 | 10/2006 | Goode et al. |
| 2006/0247751 A1 | 11/2006 | Seifert |
| 2006/0253179 A1 | 11/2006 | Goode et al. |
| 2006/0265042 A1 | 11/2006 | Catanese et al. |
| 2006/0276871 A1 | 12/2006 | Lamson et al. |
| 2006/0287574 A1 | 12/2006 | Chin |
| 2007/0015964 A1 | 1/2007 | Eversull et al. |
| 2007/0016130 A1 | 1/2007 | Leeflang et al. |
| 2007/0021812 A1 | 1/2007 | Manning et al. |
| 2007/0049929 A1 | 3/2007 | Catanese et al. |
| 2007/0050003 A1 | 3/2007 | Zarembo et al. |
| 2007/0078500 A1 | 4/2007 | Ryan |
| 2007/0083217 A1 | 4/2007 | Eversull et al. |
| 2007/0100410 A1 | 5/2007 | Lamson et al. |
| 2007/0106328 A1 | 5/2007 | Wardle et al. |
| 2007/0129710 A1 | 6/2007 | Rudko et al. |
| 2007/0142846 A1 | 6/2007 | Catanese et al. |
| 2007/0197861 A1 | 8/2007 | Reiley et al. |
| 2007/0198020 A1 | 8/2007 | Reiley et al. |
| 2007/0232981 A1 | 10/2007 | Ravenscroft et al. |
| 2007/0276412 A1 | 11/2007 | Catanese et al. |
| 2007/0293853 A1 | 12/2007 | Truckal et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0015625 A1 | 1/2008 | Ventura et al. |
| 2008/0021484 A1 | 1/2008 | Catanese et al. |
| 2008/0021485 A1 | 1/2008 | Catanese et al. |

(56) References Cited

U.S. PATENT DOCUMENTS

| | | |
|---|---|---|
| 2008/0033232 A1 | 2/2008 | Catanese et al. |
| 2008/0033456 A1 | 2/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039876 A1 | 2/2008 | Catanese et al. |
| 2008/0039889 A1 | 2/2008 | Lamson et al. |
| 2008/0039893 A1 | 2/2008 | McLean et al. |
| 2008/0039894 A1 | 2/2008 | Catanese et al. |
| 2008/0045986 A1 | 2/2008 | To et al. |
| 2008/0051756 A1 | 2/2008 | Makower et al. |
| 2008/0058759 A1 | 3/2008 | Makower et al. |
| 2008/0071341 A1 | 3/2008 | Goode et al. |
| 2008/0071342 A1 | 3/2008 | Goode et al. |
| 2008/0097378 A1 | 4/2008 | Zuckerman |
| 2008/0097426 A1 | 4/2008 | Root et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0125634 A1 | 5/2008 | Ryan et al. |
| 2008/0125748 A1 | 5/2008 | Patel |
| 2008/0147061 A1 | 6/2008 | Goode et al. |
| 2008/0154293 A1 | 6/2008 | Taylor |
| 2008/0154296 A1 | 6/2008 | Taylor et al. |
| 2008/0183163 A1 | 7/2008 | Lampropoulos et al. |
| 2008/0194969 A1 | 8/2008 | Werahera |
| 2008/0195128 A1* | 8/2008 | Orbay ............ A61B 17/320016 600/183 |
| 2008/0208105 A1 | 8/2008 | Zelickson et al. |
| 2008/0221560 A1 | 9/2008 | Arai et al. |
| 2008/0228208 A1 | 9/2008 | Wulfman et al. |
| 2008/0249516 A1 | 10/2008 | Muenker |
| 2008/0262516 A1 | 10/2008 | Gambale et al. |
| 2008/0275497 A1 | 11/2008 | Palmer et al. |
| 2008/0275498 A1 | 11/2008 | Palmer et al. |
| 2008/0281308 A1 | 11/2008 | Neuberger et al. |
| 2008/0287888 A1 | 11/2008 | Ravenscroft |
| 2008/0306333 A1 | 12/2008 | Chin |
| 2009/0012510 A1 | 1/2009 | Bertolero et al. |
| 2009/0018523 A1 | 1/2009 | Lamson et al. |
| 2009/0018553 A1 | 1/2009 | McLean et al. |
| 2009/0034927 A1 | 2/2009 | Temelkuran et al. |
| 2009/0036871 A1 | 2/2009 | Hayase et al. |
| 2009/0054918 A1 | 2/2009 | Henson |
| 2009/0060977 A1 | 3/2009 | Lamson et al. |
| 2009/0071012 A1 | 3/2009 | Shan et al. |
| 2009/0076522 A1 | 3/2009 | Shan |
| 2009/0131907 A1 | 5/2009 | Chin et al. |
| 2009/0157045 A1 | 6/2009 | Haarala et al. |
| 2009/0182313 A1 | 7/2009 | Auld |
| 2009/0187196 A1 | 7/2009 | Vetter |
| 2009/0192439 A1 | 7/2009 | Lamson et al. |
| 2009/0198098 A1 | 8/2009 | Okada |
| 2009/0204128 A1 | 8/2009 | Lamson et al. |
| 2009/0221994 A1 | 9/2009 | Neuberger et al. |
| 2009/0222025 A1 | 9/2009 | Catanese et al. |
| 2009/0227999 A1 | 9/2009 | Willis et al. |
| 2009/0234378 A1 | 9/2009 | Escudero et al. |
| 2009/0319015 A1 | 12/2009 | Horn-Wyffels |
| 2010/0004606 A1 | 1/2010 | Hansen et al. |
| 2010/0016836 A1 | 1/2010 | Makower et al. |
| 2010/0030154 A1 | 2/2010 | Duffy |
| 2010/0030161 A1 | 2/2010 | Duffy |
| 2010/0030262 A1 | 2/2010 | McLean et al. |
| 2010/0030263 A1 | 2/2010 | Cheng et al. |
| 2010/0049225 A1 | 2/2010 | To et al. |
| 2010/0063488 A1 | 3/2010 | Fischer et al. |
| 2010/0125253 A1 | 5/2010 | Olson et al. |
| 2010/0137873 A1 | 6/2010 | Grady et al. |
| 2010/0160952 A1 | 6/2010 | Leeflang et al. |
| 2010/0191165 A1 | 7/2010 | Appling et al. |
| 2010/0198194 A1 | 8/2010 | Manning et al. |
| 2010/0198229 A1 | 8/2010 | Olomutzki et al. |
| 2010/0217277 A1 | 8/2010 | Truong |
| 2010/0222737 A1 | 9/2010 | Arnold et al. |
| 2010/0222787 A1 | 9/2010 | Goode et al. |
| 2010/0240951 A1 | 9/2010 | Catanese et al. |
| 2010/0256616 A1 | 10/2010 | Katoh et al. |
| 2010/0268175 A1 | 10/2010 | Lunsford |
| 2010/0280496 A1 | 11/2010 | Shippert |
| 2010/0324472 A1 | 12/2010 | Wulfman |
| 2010/0331793 A1 | 12/2010 | Tulleken |
| 2011/0004238 A1 | 1/2011 | Palmer et al. |
| 2011/0009957 A1 | 1/2011 | Langberg et al. |
| 2011/0022057 A1 | 1/2011 | Eigler et al. |
| 2011/0028959 A1 | 2/2011 | Chasan |
| 2011/0034790 A1 | 2/2011 | Mourlas et al. |
| 2011/0040238 A1 | 2/2011 | Wulfman et al. |
| 2011/0040312 A1 | 2/2011 | Lamson et al. |
| 2011/0040315 A1 | 2/2011 | To et al. |
| 2011/0040326 A1 | 2/2011 | Wei et al. |
| 2011/0046648 A1 | 2/2011 | Johnston et al. |
| 2011/0054493 A1 | 3/2011 | McLean et al. |
| 2011/0060349 A1 | 3/2011 | Cheng et al. |
| 2011/0071440 A1 | 3/2011 | Torrance et al. |
| 2011/0105947 A1 | 5/2011 | Fritscher-Ravens et al. |
| 2011/0106004 A1 | 5/2011 | Eubanks et al. |
| 2011/0106099 A1 | 5/2011 | Duffy et al. |
| 2011/0112548 A1 | 5/2011 | Fifer et al. |
| 2011/0112562 A1 | 5/2011 | Torrance |
| 2011/0112563 A1 | 5/2011 | To et al. |
| 2011/0112564 A1 | 5/2011 | Wolf |
| 2011/0118660 A1 | 5/2011 | Torrance et al. |
| 2011/0144423 A1 | 6/2011 | Tong et al. |
| 2011/0144425 A1 | 6/2011 | Catanese et al. |
| 2011/0151463 A1 | 6/2011 | Wulfman |
| 2011/0152607 A1 | 6/2011 | Catanese et al. |
| 2011/0152906 A1 | 6/2011 | Escudero et al. |
| 2011/0152907 A1 | 6/2011 | Escudero et al. |
| 2011/0160747 A1 | 6/2011 | McLean et al. |
| 2011/0160748 A1 | 6/2011 | Catanese et al. |
| 2011/0166564 A1 | 7/2011 | Merrick et al. |
| 2011/0178543 A1 | 7/2011 | Chin et al. |
| 2011/0190758 A1 | 8/2011 | Lamson et al. |
| 2011/0196298 A1 | 8/2011 | Anderson et al. |
| 2011/0196355 A1 | 8/2011 | Mitchell et al. |
| 2011/0196357 A1 | 8/2011 | Srinivasan |
| 2011/0208207 A1 | 8/2011 | Bowe et al. |
| 2011/0213398 A1 | 9/2011 | Chin et al. |
| 2011/0218528 A1 | 9/2011 | Ogata et al. |
| 2011/0238078 A1 | 9/2011 | Goode et al. |
| 2011/0238102 A1 | 9/2011 | Gutfinger et al. |
| 2011/0245751 A1 | 10/2011 | Hofmann |
| 2011/0257592 A1 | 10/2011 | Ventura et al. |
| 2011/0270169 A1 | 11/2011 | Gardeski et al. |
| 2011/0270170 A1 | 11/2011 | Gardeski et al. |
| 2011/0270289 A1 | 11/2011 | To et al. |
| 2011/0300010 A1 | 12/2011 | Jarnagin et al. |
| 2011/0301417 A1 | 12/2011 | Mourlas et al. |
| 2011/0301626 A1 | 12/2011 | To et al. |
| 2012/0035590 A1 | 2/2012 | Whiting et al. |
| 2012/0041422 A1 | 2/2012 | Whiting et al. |
| 2012/0053564 A1 | 3/2012 | Ravenscroft |
| 2012/0065466 A1 | 3/2012 | Slater |
| 2012/0065659 A1 | 3/2012 | To |
| 2012/0083810 A1 | 4/2012 | Escudero et al. |
| 2012/0083826 A1 | 4/2012 | Chao et al. |
| 2012/0095447 A1 | 4/2012 | Fojtik |
| 2012/0095479 A1 | 4/2012 | Bowe et al. |
| 2012/0097174 A1 | 4/2012 | Spotnitz et al. |
| 2012/0123411 A1 | 5/2012 | Ibrahim et al. |
| 2012/0136341 A1 | 5/2012 | Appling et al. |
| 2012/0165827 A1 | 6/2012 | Khairkhahan et al. |
| 2012/0165861 A1 | 6/2012 | Palmer et al. |
| 2012/0191015 A1 | 7/2012 | Zannis et al. |
| 2012/0209173 A1 | 8/2012 | Hayase et al. |
| 2012/0215305 A1 | 8/2012 | Le et al. |
| 2012/0239008 A1 | 9/2012 | Fojtik |
| 2012/0245600 A1 | 9/2012 | McLean et al. |
| 2012/0253229 A1 | 10/2012 | Cage |
| 2012/0265183 A1 | 10/2012 | Tulleken et al. |

(56) References Cited

U.S. PATENT DOCUMENTS

| | | | |
|---|---|---|---|
| 2012/0323252 A1 | 12/2012 | Booker | |
| 2012/0323253 A1 | 12/2012 | Garai et al. | |
| 2012/0330292 A1 | 12/2012 | Shadduck et al. | |
| 2013/0006228 A1 | 1/2013 | Johnson et al. | |
| 2013/0035676 A1 | 2/2013 | Mitchell et al. | |
| 2013/0085486 A1 | 4/2013 | Boutoussov et al. | |
| 2013/0096582 A1 | 4/2013 | Cheng et al. | |
| 2013/0103047 A1 | 4/2013 | Steingisser et al. | |
| 2014/0031800 A1 | 1/2014 | Ben Oren et al. | |
| 2014/0081252 A1 | 3/2014 | Bowe et al. | |
| 2014/0081289 A1 | 3/2014 | Fiser | |
| 2014/0081303 A1 | 3/2014 | Bowe et al. | |
| 2014/0081304 A1 | 3/2014 | Bowe et al. | |
| 2014/0081306 A1 | 3/2014 | Bowe et al. | |
| 2014/0081367 A1 | 3/2014 | Hendrick et al. | |
| 2014/0275982 A1 | 9/2014 | Hendrick et al. | |
| 2014/0276682 A1 | 9/2014 | Hendrick et al. | |
| 2014/0276683 A1 | 9/2014 | Hendrick et al. | |
| 2014/0276694 A1 | 9/2014 | Hendrick et al. | |
| 2014/0276695 A1 | 9/2014 | Burton | |
| 2014/0276696 A1 | 9/2014 | Schneider | |
| 2014/0276920 A1 | 9/2014 | Hendrick et al. | |
| 2014/0277037 A1 | 9/2014 | Grace et al. | |
| 2016/0022303 A1 | 1/2016 | Fiser | |
| 2016/0338727 A1 | 11/2016 | Bowe | |
| 2017/0325835 A1 | 11/2017 | Bowe | |
| 2017/0340346 A1 | 11/2017 | Hendrick | |

FOREIGN PATENT DOCUMENTS

| | | | |
|---|---|---|---|
| JP | 2004516073 A | 6/2004 | |
| WO | 1991006271 A | 5/1991 | |
| WO | 1991017711 A1 | 11/1991 | |
| WO | 1993018818 A1 | 9/1993 | |
| WO | 1995033513 A1 | 12/1995 | |
| WO | 1999007295 A1 | 2/1999 | |
| WO | 1999049937 A1 | 10/1999 | |
| WO | 1999058066 A1 | 11/1999 | |
| WO | 2001076680 A1 | 10/2001 | |
| WO | 2002049690 A9 | 5/2003 | |
| WO | 2004049956 A2 | 6/2004 | |
| WO | 2004080345 A2 | 9/2004 | |
| WO | 2004080507 A2 | 9/2004 | |
| WO | 2006007410 A2 | 1/2006 | |
| WO | 2008005888 A2 | 1/2008 | |
| WO | 2008005891 A2 | 1/2008 | |
| WO | 2008042987 A2 | 4/2008 | |
| WO | 2009005779 A1 | 1/2009 | |
| WO | 2009054968 A1 | 4/2009 | |
| WO | 2009065082 A1 | 5/2009 | |
| WO | 2009126309 A2 | 10/2009 | |
| WO | 2011003113 A1 | 1/2011 | |
| WO | 2011084863 A2 | 7/2011 | |
| WO | 2011133941 A2 | 10/2011 | |
| WO | 2011162595 A1 | 12/2011 | |
| WO | 2012009697 A4 | 4/2012 | |
| WO | 2012098335 A1 | 7/2012 | |
| WO | 2012114333 A1 | 8/2012 | |
| WO | 2012177117 A1 | 12/2012 | |
| WO | 2013036588 A1 | 3/2013 | |

OTHER PUBLICATIONS

Papaioannou, T., et al. Excimer Laser (308 nm) Recanalisation of In-Stent Restenosis: Thermal Considerations, Lasers Med Sci., 16(2):90-100, 2001. [Abstract Only].
St. Luke's Roosevelt Hospital Center. Laser Lead Extraction. Arrhythmia News, 11(2), 3 pages, 2006.
Department of Health and Ageing in Australian Government, "Horizon Scanning Technology Prioritising: Laser Extraction Systems." 2010. 15 pages.
International Preliminary Examination Report issued in PCT/US2013/059434, completed Mar. 26, 2015, 11 pages.
International Preliminary Examination Report issued in PCT/US2013/059448, completed Mar. 26, 2015, 9 pages.
International Search Report and Written Opinion issued in PCT/US2013/059448, dated Dec. 16, 2013, 12 pages.
Kennergren et al. "Laser-Assisted Lead Extraction: the European Experience." Europace. 2007, vol. 9, No. 8. 6 pages.
Wilkoff, Bruce et al. "Pacemaker Lead Extraction with the Laser Sheath: Results of the Pacing Lead Extraction with the Excimer Sheath (Plexes) Trial." Journal of the American College of Cardiology, 1999. vol. 33, No. 6. 8 pages.
Decision to Grant for European Patent Application No. 07255018.9, dated Aug. 8, 2013, 2 pages.
Extended European Search Report for European Application No. 07255018.9, dated Nov. 12, 2010.
Final Action for U.S. Appl. No. 11/615,005, dated Nov. 9, 2009, 10 pages.
Final Action for U.S. Appl. No. 11/615,005, dated Nov. 21, 2013, 20 pages.
Final Action for U.S. Appl. No. 11/615,006 dated Oct. 26, 2009, 9 pages.
Intent to Grant for European Patent Application No. 07255018.9, dated Nov. 29, 2012, 7 pages.
International Search Report and Written Opinion for International Patent Application No. PCT/US2013/059434, dated Dec. 13, 2013, 14 pages.
Notice of Allowance for European Patent Application No. 07255018.9, dated Jul. 26, 2012, 47 pages.
Notice of Allowance for Japan Patent Application No. 2007-333273, dated Jan. 16, 2014, 3 pages.
Official Action for European Application No. 07255019.7, dated Jul. 21, 2010 4 pages.
Official Action for European Patent Application No. 07255018.9, dated Jul. 19, 2011, 3 pages.
Official Action for U.S. Appl. No. 11/615,005, dated Apr. 16, 2009, 13 pages.
Official Action for U.S. Appl. No. 11/615,005, dated Feb. 11, 2011, 12 pages.
Official Action for U.S. Appl. No. 11/615,005, dated Jul. 21, 2010, 10 pages.
Official Action for U.S. Appl. No. 11/615,005, dated Mar. 14, 2013, 16 pages.
Official Action for U.S. Appl. No. 13/800,728, dated Jan. 16, 2014, 14 pages.
Official Action for U.S. Appl. No. 11/615,006 dated Apr. 24, 2009, 7 pages.
Official Action for U.S. Appl. No. 11/615,006 dated Feb. 17, 2010, 8 pages.
Official Action for U.S. Appl. No. 11/615,006 dated Jul. 20, 2010, 9 pages.
Official Action for U.S. Appl. No. 11/615,006 dated Mar. 14, 2013, 16 pages.
Official Action for U.S. Appl. No. 11/615,006 dated Nov. 22, 2013, 16 pages.
Official Action with English translation for Japan Patent Application No. 2007-333173, dated Apr. 30, 2013, 5 pages.
Official Action with English translation for Japan Patent Application No. 2007-333173, dated Aug. 13, 2012, 7 pages.
Extended European Search Report issued in EP application 13837908, dated May 5, 2016, 6 pages.

* cited by examiner

DISTAL END SUPPORTED TISSUE SLITTING APPARATUS

CROSS REFERENCE TO RELATED APPLICATIONS

The present application is a continuation of U.S. patent application Ser. No. 14/192,445, filed on Feb. 27, 2014, which claims the benefits of and priority, under 35 U.S.C. § 119(e), to U.S. Provisional Application Ser. No. 61/784,203, filed on Mar. 14, 2013, entitled "Distal End Supported Tissue Slitting Apparatus," the entire disclosure of which is hereby incorporated herein by reference, in its entirety, for all that it teaches and for all purposes.

This application is also related to U.S. patent application Ser. No. 13/828,231, filed on Mar. 14, 2013, entitled, "Tissue Slitting Methods and Systems"; Ser. No. 13/828,310, filed on Mar. 14, 2013, entitled, "Tissue Slitting Methods and Systems"; Ser. No. 13/828,383, filed on Mar. 14, 2013, entitled, "Tissue Slitting Methods and Systems"; Ser. No. 13/828,441, filed on Mar. 14, 2013, entitled, "Tissue Slitting Methods and Systems"; Ser. No. 13/828,638, filed on Mar. 14, 2013, entitled, "Lead Removal Sleeve" and Ser. No. 13/828,536, filed on Mar. 14, 2013, entitled, "Expandable Lead Jacket". The entire disclosures of the applications listed above are hereby incorporated herein by reference, in their entirety, for all that they teach and for all purposes.

FIELD OF THE DISCLOSURE

The present disclosure relates generally to devices, methods and systems for separating tissue in a patient, and more specifically, to techniques for separating tissue attached to leads in a patient.

BACKGROUND

Cardiac pacing systems typically include a pacemaker and one or more leads, which are placed inside the body of a patient. The pacemaker includes a power source and circuitry configured to send timed electrical pulses to the lead. The lead carries the electrical pulse to the heart to initiate a heartbeat, and transmits information about the heart's electrical activity to the pacemaker. The lead can include a fixation mechanism that holds the lead to the cardiac tissue. In some cases, a lead is inserted through a vein or artery (collectively vasculature) and guided to the heart where it is attached. In other instances, a lead is attached to the outside of the heart. During its time in the body, tissue can attach to the lead in the form of lesions, adhesions or scar tissue, or tissue can encase a lead. In addition, the lead and/or tissue can become attached to the vasculature wall. At times, leads may be removed from patients for numerous reasons, including but not limited to, infections, lead age, and lead malfunction. Accordingly, removal or extraction of the lead may present associated complications.

Current lead extraction techniques include mechanical traction, mechanical devices, and laser devices. Mechanical traction can be accomplished by inserting a locking stylet into the hollow portion of the lead and then pulling the lead to remove it. An example of such a lead locking device is described and illustrated in U.S. Pat. No. 6,167,315 to Coe et al., which is hereby incorporated herein by reference in its entirety for all that it teaches and for all purposes. In some cases, dilating telescopic sheaths may also be used to strip away the scar tissue adhering the lead to the body. Examples of a such devices and methods used to extract leads is described and illustrated in United States Patent Publication No. 2008/0154293 to Taylor, which is hereby incorporated herein by reference in its entirety for all that it teaches and for all purposes.

Dilation techniques typically involve pushing tissue away from the lead when the sheath is pushed longitudinally along the lead. However, this pushing technique may be difficult to implement, particularly when the lead has a tortuous path or curvature because the requisite longitudinal forces to extract the tissue from the lead in under these circumstances increase. The longitudinal forces also may require heavy counter forces on the lead, which may result in lead breakage.

Some mechanical sheaths have proposed trigger mechanisms for extending a blade from a sheath. At least some of these devices, however, involve complicated activation mechanisms and may not be well suited for negotiating the tortuous paths that exist in certain vascular or physiological environments.

Laser devices typically employ laser energy to cut the scar tissue away from the lead thus allowing for removal. Examples of such laser devices and systems are described and illustrated in U.S. Pat. Nos. 5,383,199 and 5,824,026 and 5,916,210 and 6,228,076 and 6,290,668 all of which are hereby incorporated herein by reference in their entirety for all that they teach and for all purposes.

Further complicating lead removal is the fact that in some cases, the leads may be located in, and/or attached to, the body of a patient in a structurally-weak portion of the vasculature. For instance, typical leads in a human may pass through the innominate vein, past the superior vena cava ("SVC"), and into the right atrium of the heart. A majority of tissue growth can occur along the SVC and other locations along the innominate vein where the leads make contact with the vein walls. However, tissue growth can also occur at locations within a patient where the leads make contact with arterials or other areas of the vasculature. Certain veins and arteries, and certain areas of vein and arterial walls, can be thin which can make lead removal a complicated and delicate process.

SUMMARY

A traditional approach to removing tissue from implanted leads is based on the presumption that the tissue growths are adhered directly to the surfaces of the implanted leads. As such, methods and systems have been designed to dislocate the connection between the tissue attached to the implanted device and the body of a patient. Although some tissue may remain on the lead, current methods focus on removing most of the tissue surrounding a circumference of the lead. In other words, while tissue may remain attached around the lead, current systems essentially core around this tissue surrounding the circumference of a lead to free the lead along with a section of the cored tissue to create slack for removing the lead from a patient.

Surprisingly and unexpectedly, it has been discovered that tissue growth may not adhere directly to the implanted lead but actually form a substantially cylindrical "tube" around the implanted substantially cylindrical lead at a given contact area. Contrary to conventional wisdom, the tissue growth typically does not physically adhere to the lead. For example, this tissue growth, once formed completely around a lead, forms a tubular-shaped member that essentially holds the lead and resists lead removal. The tubular-shaped section of formed tissue around an implanted device may impart a combination of connection forces/modes that prevent the removal of the device from a patient. For example, the tubular-shaped section of formed tissue, or tissue growth, may constrict, capture, and/or surround implanted leads. In some cases, the tissue growth may constrict a lead, especially if a force is applied to one end of the lead during a removal operation. In other cases, the tissue growth may capture the lead and prevent removal, by, among other things, being attached to the patient and the lead simultaneously. Additionally or alternatively, the tissue growth, during attempted lead removal, may at least partially adhere to the lead in one or more sections while completely forming around the lead.

Based upon the surprising and unexpected discovery that tissue growth may not be directly adhered to the implanted lead, alternative devices and methods may be used to extract an object from such tissue. In other words, methods and devices are disclosed herein, that are capable of exploiting the growth nature of the tissue around a lead to efficiently extract the lead from tissue that acts to hold the lead with some type of force. The tissue growth may form around the lead such that the lead is contained from free movement within a patient. For instance, the tissue growth may impart a clamping, or constrictive, force around the circumference of the lead that can prevent movement of the lead within this constrictive tissue growth. Due to the taught and constrictive nature of the tissue around the lead, the lead may be able to be removed without mechanically removing or laser ablating the entire tissue region surrounding the lead in a 360 degree, or circumferential, fashion. Rather, initiating a cut and/or slit of the tissue along a longitudinal axis of the lead may allow a surgeon to easily separate the lead from the tissue via the slit. For example, once the tissue is initially slit, a surgeon may be able to extract the lead from the tissue, by pulling the lead with the use of a lead locking, or similar, device. This lead extraction may be made possible by the initial slit reducing the restrictive forces caused by tissue growth in a given area. Lead extraction may also be effected by moving the lead against the initial slit created to tear through the tissue growth.

The tissue growth may need to be slit or cut along an entire length of tissue growth such that the tissue growth is no longer capable of imparting clamping, or constrictive, forces around the lead. Once the tissue growth is slit along its length, removal of the lead from the section of tissue growth can be achieved using various lead removal techniques, including but not limited to, traction/counter-traction applied to the lead and growth, lead locking devices, snares, sheath insertion, moving the lead against the slit portion of the tissue, and the like.

Accordingly, there is a need for a device, method and/or system such as a device that includes a tissue slitting or cutting edge that facilitates slitting a length of formed tissue surrounding a lead, and optionally a method and system capable of removing the lead from the formed tissue that captures at least a portion of an implanted lead.

The method can include the steps of cutting only a portion of a tissue growth at least substantially surrounding an implanted object in a patient and thereafter removing the implanted object. In embodiments disclosed herein, the tissue growth may be subjected to a slitting action about a partial (i.e., not complete) periphery of an internal diameter of the tissue growth. In some embodiments, the tissue growth portion cut can be no more than about 50% of a perimeter of the tissue growth adjacent to and surrounding, substantially or completely, the implanted object at any point along an encased length of the implanted object.

The tissue slitting edge may include sharpened area, point, or blade, in a static fixed and/or dynamically deployable configuration. Additionally or alternatively, the tissue slitting edge may utilize grinding mechanisms to cause a slit in the formed tissue. Additionally or alternatively, the tissue slitting edge may utilize emitted energy, such as light, thermal energy, electromagnetic energy, and/or high-pressure fluid emission to cause a slit in the formed tissue. The tissue slitting edge can be an energy device, such as a power sheath, which typically applies a form of energy at the sheath tip to cut the scar tissue away from the lead thus allowing for removal. As the sheath is pushed over the lead and comes to an area of attachment, the operator can turn on the sheath's energy source to heat or vaporize scar tissue, forming the desired slit. One of these specialized sheaths uses electrocautery, similar to what is used to cut through tissue in surgery. Another sheath has one or more tiny lasers at its tip or edge. When activated, the lasers vaporize water molecules in scar tissue within 1 mm, forming the desired slit or cut. Additionally or alternatively, dilating telescopic sheaths or inflatable balloons having a longitudinally positioned tissue slitting edge can be expanded, thereby deploying the tissue slitting edge to form the desired slit.

Accordingly, slitting devices (e.g., in the form of knife-edges, blades, planers, lasers and other electromagnetic radiation emitters, high-pressure fluid, grinders, sanders, drills, RF devices, ultrasonic devices, and the like) can be configured in various combinations and methods by which formed tissue can be removed from an implanted lead subjected to any combination of connection modes via the formed tissue.

Removal of the formed tissue, or tissue growth, from a lead may be effected by creating a slit, or cut, along a length of the tissue growth. By slitting the formed tissue along an axial portion, or length, of the tissue connected to the surgically implanted device or surgical implant, it is anticipated that the connection to the implanted lead will be severely weakened. In many cases, the tissue slitting device may allow the implanted lead to essentially peel away from the tissue previously surrounding the implanted lead, thereby releasing it from containment. These and other needs are addressed by the various aspects, embodiments, and/or configurations of the present disclosure. Also, while the disclosure is presented in terms of exemplary embodiments, it should be appreciated that individual aspects of the disclosure can be separately claimed.

The tissue slitting device includes a flexible shaft having a proximal end, a distal end, and an internal lumen having an internal diameter configured to allow a lead, lead locking device, and/or other implanted device to pass through it. The device may also include a tissue slitting tip operatively coupled with the distal end of the flexible shaft. As can be appreciated, the slitting of formed tissue can be performed by at least one of cutting, drilling, slicing, stripping, chopping, sanding, grinding, planning, abrasion, high-pressure fluid, laser ablation, and combinations thereof. It is anticipated that the tissue slitting device may be oriented within a patient via use of the flexible shaft and monitor, or a catheter-based system. In some cases, the tissue slitting device may be positioned toward the center of the vasculature, and/or proximal to a non-traumatic leading edge, such that any sharp, or working, edge is caused to contact tissue growth and not contact the vasculature.

Among other things, the slitting section of the tissue slitting device may be biased against a lead/object via spring force. Additionally or alternatively, the tissue slitting device may include a flexible portion configured to allow the tissue slitting device to move as directed within a patient.

In has been further discovered that an efficient technique for slitting tissue growth surrounding an implanted lead involves cutting the tissue from an inner portion of the tissue growth to an outer portion of the tissue growth. The inner portion may correspond to a diameter of the tissue growth that is in contact with the lead, while the outer portion of the tissue growth may be an area adjacent to an external surface of the tissue growth, where the external surface is free from attachment to the vessel wall. This action may be similar to inserting a sharpened edge and point of a knife into a tissue growth at the internal diameter of the tissue growth and then moving the blade outwardly away from the internal diameter to cause a slit in the tissue growth. Among other things, this slitting action may place the tissue fibers under tension as the sharpened edge and point of the knife engages with and/or moves into the tissue growth in a direction away from the surface of the lead. Once the tissue is slit, the tension of the tissue fibers may be released in the slitting area. Various shapes of the slitting element may assist in the slitting action (e.g., curved, linear, compound, interrupted, serrated, sinusoidal, etc.). Additionally or alternatively, the slitting element may be configured to present a sharpened edge to the tissue, while a flat or dull edge (e.g., unsharpened) may contact the lead. This configuration of the slitting element may prevent undesired damage to the lead as the slitting element is moved along the lead and/or as the slitting element slits tissue. Although the motions of moving into the tissue growth and away from the lead may be separate, it is anticipated that such motions may be combined in a compound and/or concurrent motion.

The tissue slitting device may include an end support device disposed adjacent to the distal end of the flexible shaft. It is anticipated that the end support device may be configured to provide a clamping force to a lead within the vasculature of a patient. In one example, the clamping force may be used to grasp the lead and/or provide support for a tissue slitting element disposed adjacent to the end support element. The end support device may be arranged as one or more end support elements that are capable, alone or in combination, of restricting movement of the flexible shaft of the tissue slitting device. For example, the end support device may be arranged as a collet (e.g., a chuck, vise, spring collet, etc.) having a proximal and a distal end, with at least one tapered outer surface, and a collet lumen running from the proximal to the distal end of the end support device. As can be appreciated, the collet may be separated into two or more end support elements, that when subjected to an actuation force are configured to reduce an internal diameter of the collet lumen. A reduction in dimension of the internal diameter of the collet lumen may cause at least some of the actuation force to be applied as a clamping force around a lead or other implanted object in an area defined by the collet lumen. The actuation force may be applied by a directed force transmitted via an end support device lock that is configured to contact the tapered outer surface of the collet. The tapered outer surface of the collet can direct the actuation force toward the center of the collet. In other words, the collet may be closed (i.e., reducing the internal diameter of the collet lumen) from the end support device lock contacting the tapered outer surface of the collet.

In some embodiments, the one or more end support elements may be arranged as spring steel elements that are configured in a first position biased toward a center of the collet lumen. The bias of the spring steel elements may reduce a portion of the collet lumen internal diameter, such that the collet lumen internal diameter is less than an outer diameter associated with a lead, or implanted object. As a lead is run through the flexible shaft to the collet lumen of the tissue slitting device, the lead may force the spring steel elements into a second position away from the center of the collet lumen. In turn, the biasing force applied by the spring steel elements to the lead may cause at least a partial restriction of lead movement.

A cutting surface, or slitting element, of the tissue slitting device may be configured to move along with the end support device lock. In other words, the slitting element may be operatively connected to the end support device and/or the end support device lock. For example, a slitting element may be disposed proximal to the distal end of the end support device, and as the end support device lock engages the end support device, and/or closes an internal diameter of the collet lumen, the slitting element may move in a direction toward the distal end of the end support device. In some cases, the movement of the slitting element may be a ratio of the movement of the end support device lock (e.g., 4:1, 2:1, 1:1, 1:2, 1:4, 1:16, and/or ranges therebetween). Additionally or alternatively, the slitting element may be configured to move after a movement of the end support device and/or end support device lock. The movement of the slitting element may be caused by one or more of a pin and groove, cam profile, wedge, expanding member, and the like. As can be appreciated, such movements may be controlled as to speed, acceleration, distance, angle, dwell, return action, relative movement, etc. In one example, the end support device may be caused to close upon, and apply at least one clamping force to, a lead after which the slitting element may move. This movement can be achieved in a cam arrangement by providing a dwell for the slitting element at a first section of the cam profile. It is anticipated that various combinations and movements relative to the end support device may be used to achieve a distal end supported slitting action via the slitting element.

In addition, the slitting element may be operatively connected to, and arranged to pivot about, a pivot area to achieve a sweeping and/or arced cutting action of a cutting surface of the slitting element. In one embodiment, the sweeping cutting action may be achieved by moving the slitting element about a pivot area having at least one of a pivot point, flexure, flexure area, cantilevered member, four-bar mechanism, compound mechanism, and the like. As can be appreciated, the pivot area may be located distal to or proximal to a cutting surface of the slitting element. In some cases, the pivot area of the slitting element may be attached to the end support device, the end support device lock, and/or the flexible shaft of the tissue slitting apparatus. In any event, the slitting element is configured to provide at slit a region of the tissue growth by cutting into the tissue growth while the slitting element is supported by the end support device. For example, the tissue slitting device, or apparatus, may be presented adjacent to a tissue growth along a lead. The tissue slitting device may anchor to the lead via actuating the end support device. Once anchored, the slitting element may move toward and engage the tissue growth. As the tissue slitting element engages the tissue growth the slitting element may continue to move further into the tissue growth and/or provide an arced cutting action. Additionally or alternatively, the slitting element may wedge into an area between the lead and the tissue growth as it moves toward the tissue growth, and cut in an arced motion in a direction away from the lead toward an outside region of the tissue growth. This sweeping motion can allow the slitting element to first contact tissue at least partially surrounding a lead in an area where the tissue growth, and the tissue fibers, may be placed under tension. The tension of the fibers may be caused by the slitting element as it stretches the fibers away from the lead during its movement when in contact with the tissue. Among other things, the tension placed on the tissue growth fibers provide a taught area for the cutting surface to engage and cut along. In some embodiments, the slitting element may return along to a first position after a cutting action has been made. This action may be achieved via the one or more movement elements disclosed herein.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1-X_n$, $Y_1-Y_m$, and $Z_1-Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

A "lead" is a conductive structure, typically an electrically insulated coiled wire. The electrically conductive material can be any conductive material, with metals and intermetallic alloys common. The outer sheath of insulative material is biocompatible and biostable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

A "surgical implant" is a medical device manufactured to replace a missing biological structure, support, stimulate, or treat a damaged biological structure, or enhance, stimulate, or treat an existing biological structure. Medical implants are man-made devices, in contrast to a transplant, which is a transplanted biomedical tissue. In some cases implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Embodiments of the present disclosure are directed to tissue slitting or cutting devices and methods of using tissue slitting devices to remove an implanted lead from within the vascular system of a patient. Among other things, the method of removing an implanted lead from formed tissue may include causing at least a partial separation of tissue that lies along an axial length of the implanted lead. In some embodiments, the tissue may be slit or cut along an entire length of the tissue growth to enable removal of the implanted lead. In other embodiments, the tissue may be slit or cut along a section of the tissue growth to allow an implanted lead to be removed from a patient.

While the phrases "tissue slitting edge" or "tissue cutting edge" are used in this disclosure, it is not limited to a blade or other cutting surface. These phrases are further intended to encompass any modality for slitting or cutting tissue, including the various modalities discussed herein. Nonlimiting examples include not only a sharpened area, point, or blade but also an abrasive or cutting wire or fiber, atherotomes (microsurgical blades) mounted on an inflatable (cutting) balloon, a grinder, high intensity light such as produced by a laser, thermal or infrared energy, electromagnetic energy, and/or high-pressure fluid.

Figure 1:
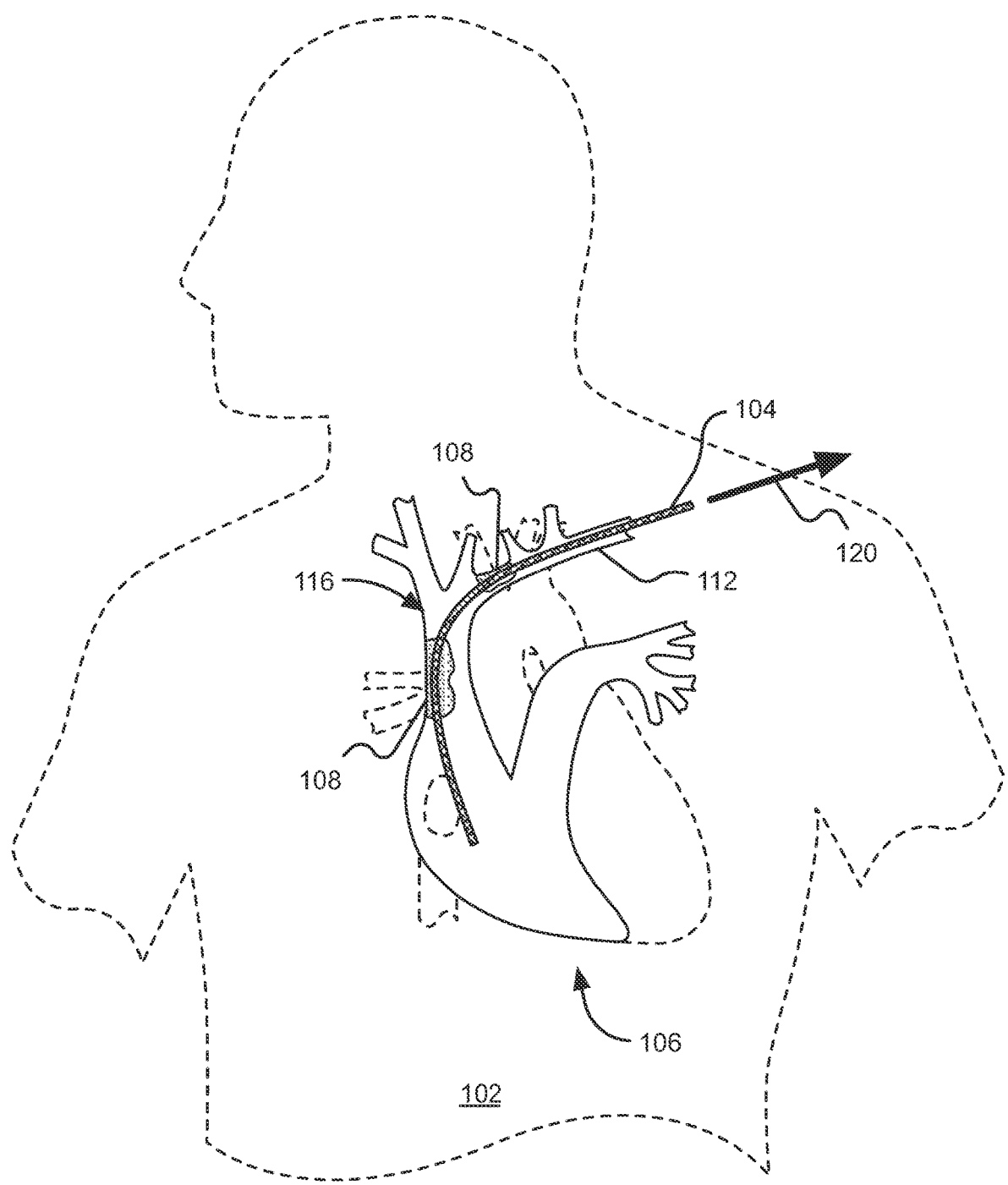
FIG. 1 shows an exemplary patient vasculature in section with implanted lead and multiple locations of tissue growth in accordance with some embodiments of the present disclosure.

FIG. 1 depicts an exemplary patient 102 with an implanted lead 104 running along the left innominate vein 112 past the superior vena cava ("SVC") and connected into, or about, the right ventricle of the heart 106. Along the length of the lead 104 at least one formed tissue growth 108 is shown where the tissue 108 may completely surround a section of the lead 104. In a typical lead 104 explant procedure, the one or more of the tissue growths 108 may act to contain the lead 104. For example, the tissue 108 may impart one or more forces (e.g., constrictive, shear, compression, and the like) on the lead 104 that may act to prevent successful removal of the lead 104 when subjected to a traction force 120.

Figure 2A:
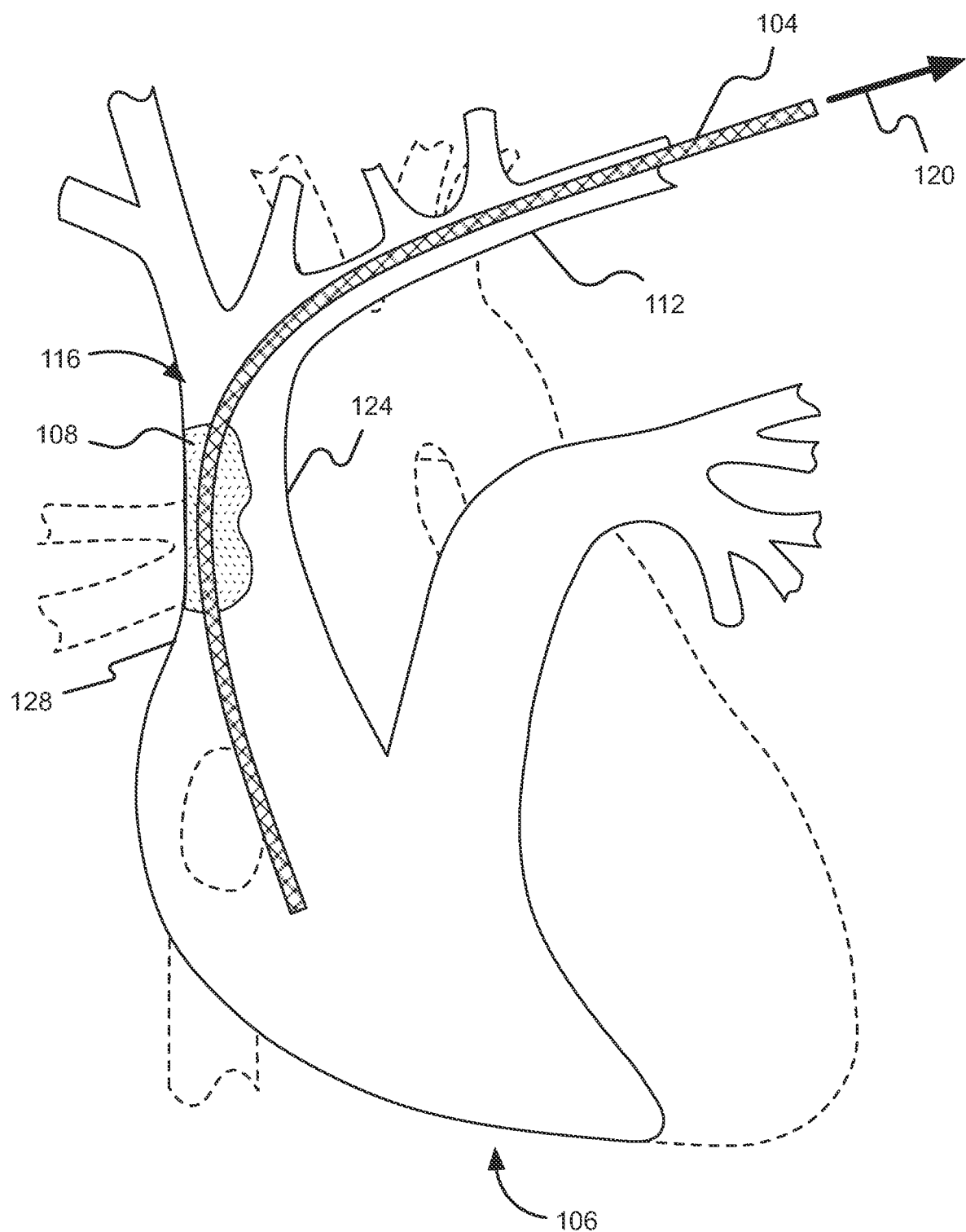
FIG. 2A shows a detail section view of a patient vasculature and implanted lead subjected to a traction force in a first path in accordance with some embodiments of the present disclosure.
Figure 2B:
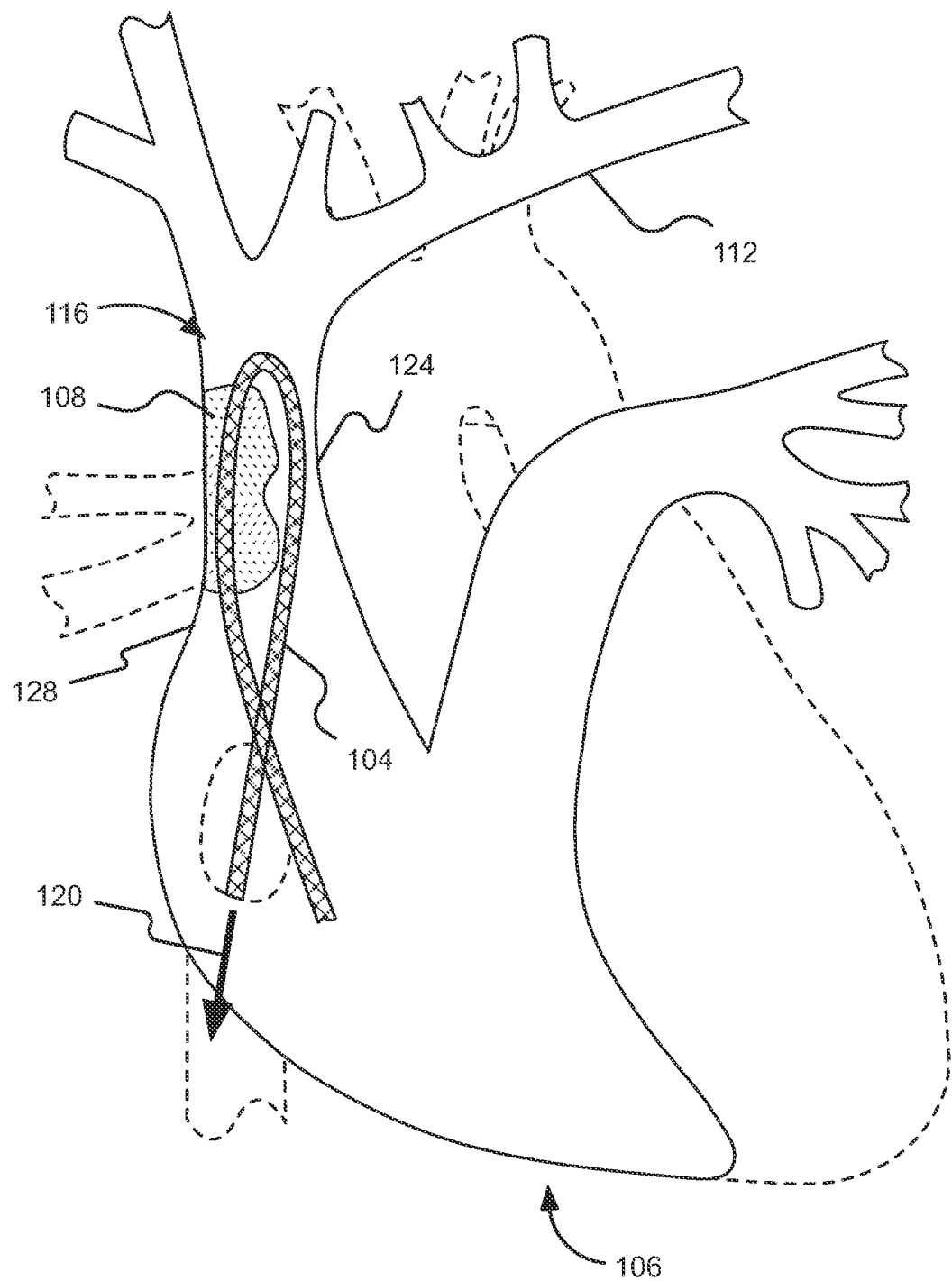
FIG. 2B shows a detail section view of a patient vasculature and implanted lead subjected to a traction force in second path in accordance with some embodiments of the present disclosure.
Figure 2C:
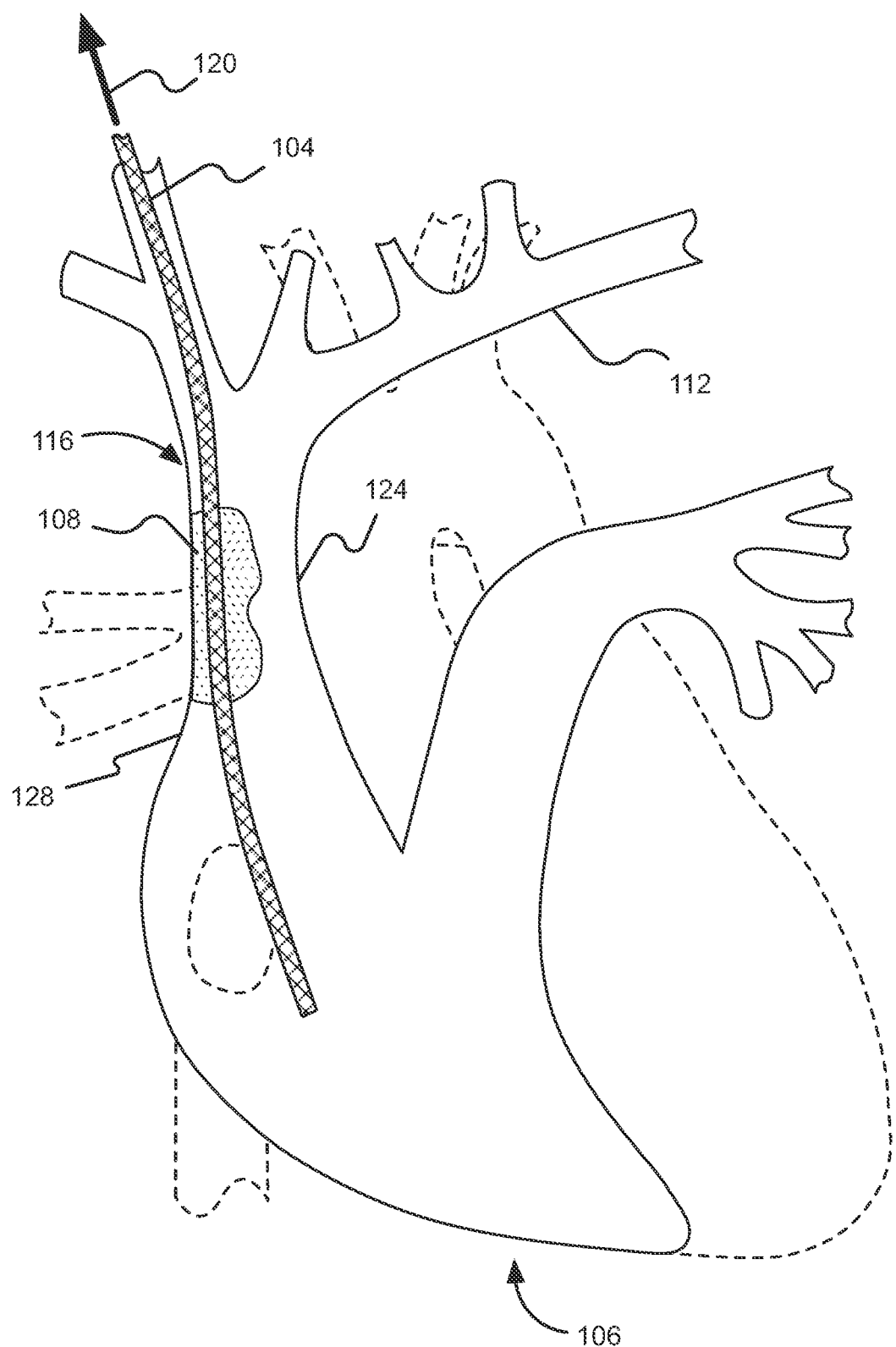
FIG. 2C shows a detail section view of a patient vasculature and implanted lead subjected to a traction force in third path in accordance with some embodiments of the present disclosure.

FIGS. 2A-C show examples of an implanted lead 104 subjected to a traction force via different paths in a patient 102 vasculature. Accordingly, the methods and/or devices disclosed in conjunction with any of the FIGS. 2A-C may equally apply to all instances disclosed.

FIG. 2A shows a detail view of a heart 106 having an implanted lead 104 subjected to a traction force 120 in a first path in accordance with embodiments of the present disclosure. In some embodiments, a lead 104 explant procedure may involve removing the lead from a patient 102 via one or more paths. For example, a lead-locking, or other traction, device may be engaged with the lead 104 and then used to pull the lead 104 from a patient. However, in some cases the lead 104 may be contained by a formed tissue growth 108 that resists the traction force 120 applied to the lead 104. As can be appreciated, subjecting the lead 104 to excessive traction forces 120 may cause a tear inside the patient 102 where the tissue is attached to the vasculature. In one example, a tissue growth 108 may form along a critical area of the vasculature, such as the SVC curve 116, of a patient. If this critical area is torn during a lead 104 explant procedure, the result can be fatal to the patient 102.

Complicating the lead 104 removal process is the fact that the tissue growth 108 surrounding a lead 104 may attach to a vessel in a curved portion of the vasculature. Removal of the lead 104 from such a curved portion of vasculature can present a challenge when introducing tissue removal devices alone or in conjunction with traction devices. In some cases, the tissue removal devices include sharp edges, aggressive tips, or imprecise actuation mechanisms that can puncture the thin walls of a patient 102 vasculature. It is an aspect of the present disclosure to orient a tissue slitting working end adjacent to the unconnected, or tissue free, side 124 of a vessel wall. This orientation can prevent puncture and/or damage occurring to the vasculature at the tissue connected side 128 of the vessel wall.

Referring now to FIG. 2B a detail section view of a patient vasculature and implanted lead 104 subjected to a traction force 120 in second path in accordance with some embodiments of the present disclosure is shown. In some instances, at least one end of the lead 104 may be directed inside a patient 102 for removal via a path within the vasculature. Direction of the lead 104 may be effected via a snaring tool, lead-locking device, traction device, combinations thereof, and the like. As shown in FIG. 2B, the lead 104 is directed toward the general direction of a patient's femoral artery via the inferior vena cava. The lead 104 may be directed in the manner shown to provide additional tearing forces on the tissue growth 108 by the lead 104 being subjected to a traction force 120. In one embodiment, the tissue growth 108 may be at least partially slit and the tearing forces created by pulling the lead 104 along the traction force 120 line cause the lead 104 to separate from the tissue growth 108. In other embodiments, a tissue slitting device may be run along the lead 104 to the tissue growth 108 via the femoral artery.

In some embodiments, the lead 104 may be captured and pulled such that the pull force causes the lead 104 to turn inside a patient 102. This mode of capture and pulling may cause a bending at a first connection point between the tissue growth 108 and the lead 104. When the tissue slitting device is engaged with the tissue growth 108, the assistive bending force provided by the traction force 120 can aid in slitting the tissue growth 108. For instance, the bending force may cause a stretching of the tissue growth 108 where the lead engages with the tissue growth 108. This stretching of tissue may assist in the slitting operation by causing tension on the fibers of the tissue growth 108 that, when slit, pull away from the tissue slitting device engagement area. As can be expected, the slitting operation may be performed in any area within a patient that is capable of receiving a tissue slitting device.

FIG. 2C shows a detail section view of a patient vasculature and implanted lead 104 subjected to a traction force 120 in third path in accordance with some embodiments of the present disclosure. Similar to FIGS. 2A and 2B, the lead 104 may be directed along a path in the patient vasculature. In this case, the lead 104 may be directed toward the general direction of a patient's jugular vein.

As can be appreciated, the path chosen for removal of a lead 104 from a patient 102 may depend on one or more of the orientation of the lead 104 within a patient 102, the state of the at least one tissue growth 108, the lead removal device used, and the tissue slitting device used. In some cases, the lead 104 (e.g., pacing, defibrillator, etc.), or other object, may have moved after implantation. In these scenarios, the lead 104 may have to be captured via some other method. In some embodiments, a capturing tool equipped with a lasso, snare, or other lead grasping element may need to be inserted into the patient 102. As can be expected, the capturing tool may be inserted into the patient 102 via any number of the veins and/or arteries that are interconnected to the lead 104 location in the vasculature. For example, the lead 104 may be grasped via a capturing tool that has been inserted through a patient's femoral artery and led to the point of the vasculature where the lead's 104 free end may be located.

In some embodiments, rather than attach a separate mechanical traction device, the capturing tool may be used to provide traction force 120 during the tissue slitting operation. In accordance with embodiments of the present disclosure, the lead may be grasped via a capturing tool, or lead-locking device, and/or removed via some other pathway in the vasculature. In other words, the lead may be accessed via one or more veins, arteries, chambers, biological channels, and/or other sections of the vasculature of a patient 102.

Figure 3:
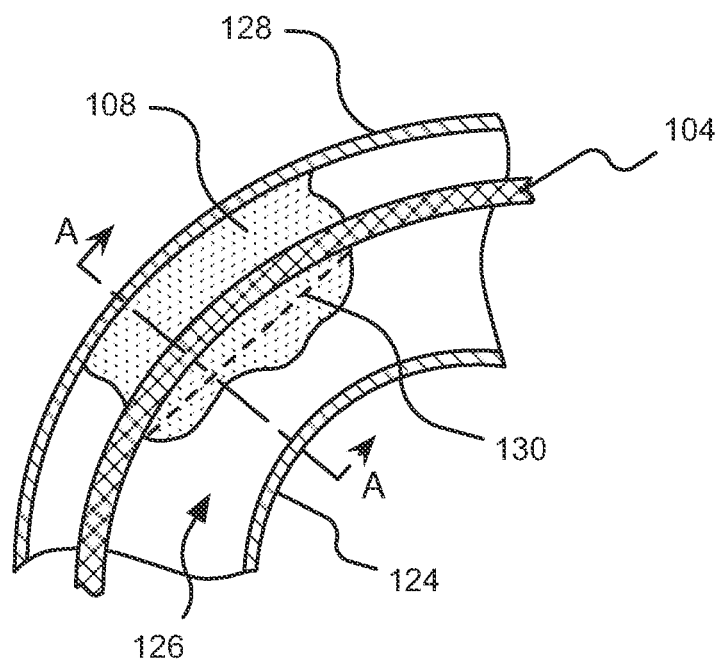
FIG. 3 shows a section view of a curved area of vasculature with tissue growth formed around an implanted lead in accordance with embodiments of the present disclosure.

FIG. 3 shows a section view of a curved area of vasculature with tissue growth 108 formed around an implanted lead 104 in accordance with embodiments of the present disclosure. The tissue growth 108 may completely surround a section of the lead 104 and even be attached to a vessel wall at a tissue connected side 128 of the vasculature. In some cases, the tissue growth 108 may not be adhered to at least one free side 124 of a vessel, such that a vessel opening 126 exists where bodily fluid may pass through the vessel unobstructed. Surprisingly and unexpectedly, it has been discovered that the tissue growth 108, before attempted lead extraction, is commonly at least substantially free of and even more commonly completely free of attachment to the lead 104.

Figure 4:
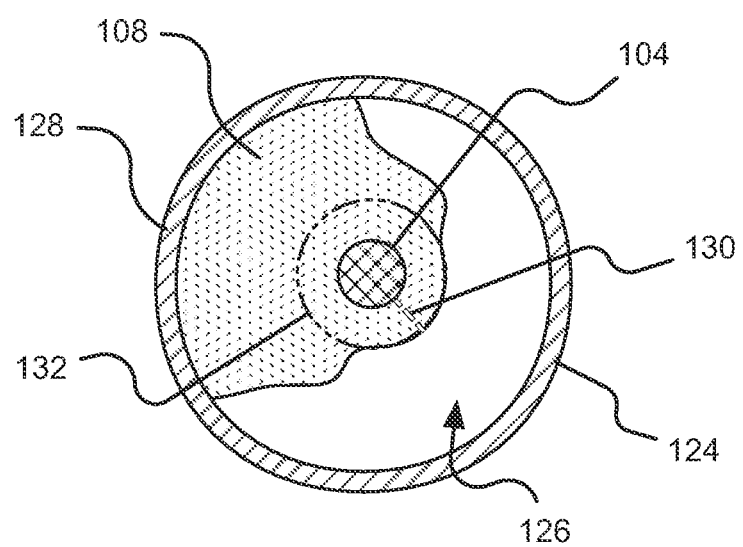
FIG. 4 shows a cross-sectional view of the curved area of vasculature of FIG. 3 taken along line A-A.

FIG. 4 shows a cross-sectional view of the curved area of vasculature of FIG. 3 taken along line A-A. In some embodiments, reference may be made to the tissue growth 108 forming a tube 132 (or cylindrical or sock-like structure) around the implanted lead 104. Previous methods have been disclosed that are directed to separating the tissue around the lead 104 in the area defined by the tube 132. It is an aspect of the present disclosure to provide one or more methods and devices to effectively separate the tissue growth 108 along a length of the lead to release the lead 104 from the containing forces of the tissue growth 108. In some embodiments, the tissue growth 108 may be slit at a portion of the tissue growth 108 where the thickness of tissue is minimal between the lead 104 and the open area 126 of the vessel.

In embodiments disclosed herein, the tissue growth 108 may be subjected to a slitting action about a partial (i.e., not complete) periphery of an internal diameter of the tissue growth 108. Stated another way, at any selected point along the tissue growth 108 or tube 132 the amount of the adjacent tissue cut or slit 130 to free the lead 104 is commonly no more than about 50%, more commonly no more than about 25%, more commonly no more than about 10%, and even more commonly no more than about 5% of the diameter of the tissue growth 108 or tube 132. The length of the cut or slit 130 in the tissue growth 108 or tube 132 is commonly at least about 50%, more commonly at least about 75%, more commonly at least about 90%, and even more commonly at least about 95% of the total length of the portion of the lead 104 surrounded by the tissue growth 108 or tube 132 along an actual and projected line of the cut or slit.

Figure 5A:
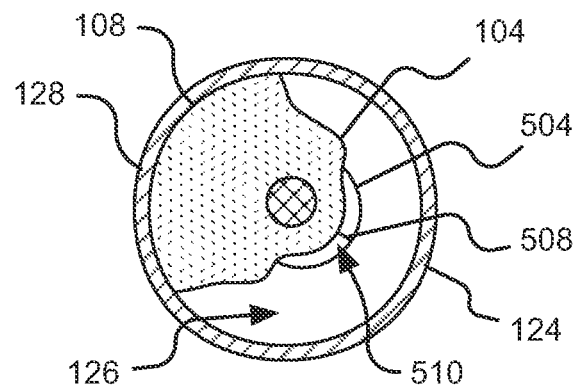
FIG. 5A shows a cross-sectional view of an area of vasculature with a tissue slitting device introduced in accordance with embodiments of the present disclosure.
Figure 5B:
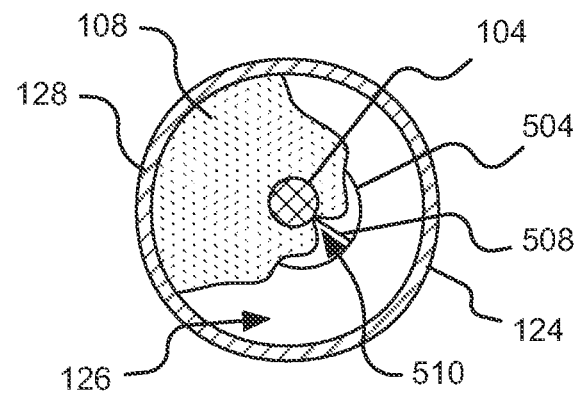
FIG. 5B shows a cross-sectional view of an area of vasculature with a tissue slitting device engaging formed tissue in accordance with embodiments of the present disclosure.
Figure 5C:
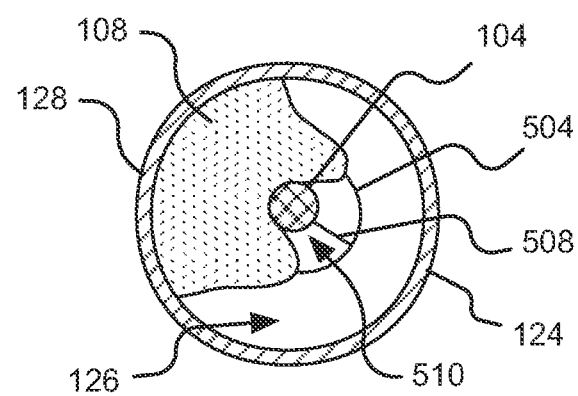
FIG. 5C shows a cross-sectional view of an area of vasculature with a tissue slitting device slitting formed tissue in accordance with embodiments of the present disclosure.

FIGS. 5A-C show a cross-section of a vessel where a tissue slitting device 504 is progressively engaged with a tissue growth 108. As shown, the tissue slitting device causes a section of the tissue growth 108 to separate from a portion of the lead 104 allowing the forces containing the lead 104 to be severely weakened and/or eliminated.

Referring to FIG. 5A a cross-sectional view of an area of vasculature with a tissue slitting device 504 introduced therein in accordance with embodiments of the present disclosure is shown. The tissue slitting device 504 includes a tissue slitting tip 508 that is configured to separate tissue growth 108. In one embodiment, the tissue slitting tip 508 may be oriented such that a slitting operation is performed on the thinnest section of tissue growth 108 between the lead 104 and the open area 126 of the vessel. Orientation of the tissue slitting device 504 may be achieved in operation via a fluoroscopy and/or other monitoring devices and the use of one or more radiopaque markers on the tissue slitting device 504. Once the tissue slitting device 504 is oriented, the tissue slitting device 504 may contact the tissue growth 108 at an engagement area 510.

In any of the embodiments disclosed herein, the tissue slitting device may include an imaging system configured to provide an image from within the vasculature of a patient 102. It is anticipated that the imaging system may be disposed adjacent to the distal tip of the tissue slitting device. Examples of such imaging systems may include, but are in no way limited to, technology incorporating Intravascular Ultrasound ("IVUS"), Optical Coherence Tomography ("OCT"), radio imaging, magnetic tracking, three-dimensional ("3D") imaging, and other technologies that may be used to obtain an image within a patient.

FIG. 5B shows a cross-sectional view of an area of vasculature with a tissue slitting device 504 engaging formed tissue 108 in accordance with embodiments of the present disclosure. As the tissue slitting device 504 engages the tissue growth 108 the tissue slitting device 504, may slit the tissue growth 108 by splitting, cutting, tearing, grinding, sanding, ablating, and/or otherwise causing a separation of tissue at the engagement area 510.

FIG. 5C shows a cross-sectional view of an area of vasculature with a tissue slitting device 504 slitting formed tissue 108 in accordance with embodiments of the present disclosure. As shown in FIG. 5C, the tissue growth 108 is separated along a section of the lead 104 about the engagement area 510. In some embodiments, the tissue slitting device may be subsequently removed from the tissue growth 108 by moving the lead 104 in the direction of the separated tissue.

FIGS. 6A-D show a section view of a curved area of vasculature where an embodiment of a tissue slitting device 604 is progressively engaged with a tissue growth 108. As shown, the tissue slitting device 604 causes a section of the tissue growth 108 to separate from a portion of the lead 104 allowing the forces containing the lead 104 to be severely weakened and/or eliminated.

Figure 6A:
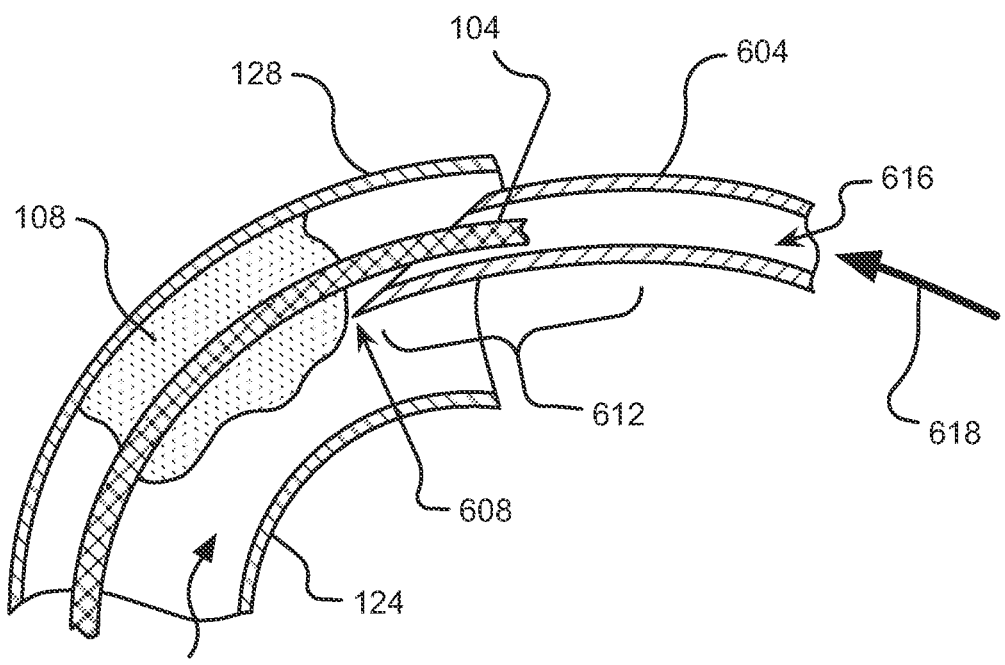
FIG. 6A shows a section view of a curved area of vasculature with a tissue slitting device first introduced in accordance with embodiments of the present disclosure.

FIG. 6A shows a section view of a curved area of vasculature with a tissue slitting device 604 first introduced in accordance with embodiments of the present disclosure. The tissue slitting device 604 is indexed into position via a directional force 618 adjacent to the tissue growth 108. The directional force 618 may be applied to the tissue slitting device 604 via one or more mechanical actuators, electrical actuators, manual positioning, and combinations thereof.

In some embodiments, the tissue slitting device 604 includes a flexible shaft having a proximal end, a distal end 612, and an internal lumen 616 having an internal diameter configured to allow a lead, lead locking device, and/or other implanted device to pass through it. The device may also include a tissue slitting tip 608 operatively attached to the distal end 612 of the flexible shaft. As can be appreciated, the slitting of formed tissue can be performed by at least one of cutting, drilling, slicing, stripping, chopping, sanding, grinding, planning, abrasion, high-pressure fluid, laser ablation, and combinations thereof. In one embodiment, the tissue slitting tip 608 of the tissue slitting device 604 may be described in conjunction with the tissue slitting apparatus 704 of FIGS. 7A-9. For example, the tissue slitting tip 608 may correspond to the slitting element 716 of the tissue slitting apparatus 704. It is anticipated that the tissue slitting device 604 may be oriented within a patient via use of the flexible shaft and monitor, or a catheter-based system. In some cases, the tissue slitting device 604 may be positioned toward the center of the vasculature, and/or proximal to a non-traumatic leading edge, such that any sharp, or working, edge is caused to contact tissue growth 108 and not contact the vasculature (e.g., the tissue connected side 128 wall and the free side 124 wall of a vessel).

Additionally or alternatively, the tissue slitting tip 608 and effective slitting section of the tissue slitting device 604 may be biased against a lead 104 via spring force. In some embodiments, the tissue slitting device 604 may include a flexible portion configured to allow the tissue slitting device 604 to move as directed within a patient.

Figure 6B:
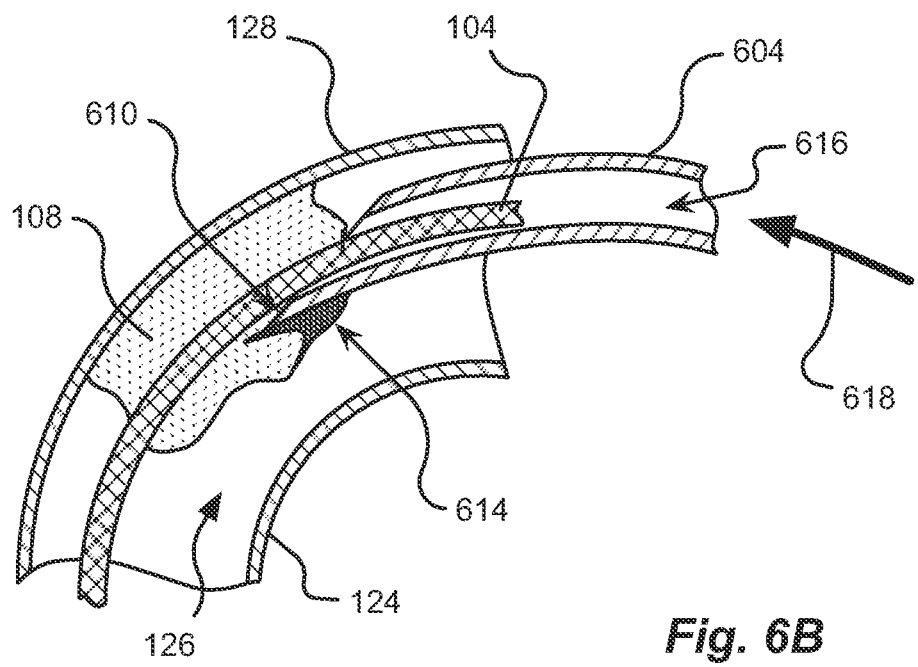
FIG. 6B shows a section view of a curved area of vasculature with a tissue slitting device in a first slitting position in accordance with embodiments of the present disclosure.

FIG. 6B shows a section view of a curved area of vasculature with a tissue slitting device 604 in a first slitting position in accordance with embodiments of the present disclosure. As the tissue slitting device 604 is directed into the tissue growth 108, the tissue slitting tip 608 causes the tissue growth 108 to separate along the engagement area 610. The separated tissue 614 allows the tissue slitting device 604 to be further engaged with the tissue growth 108. Additionally or alternatively, the separated tissue 604, by releasing forces containing the lead, can allow the lead 104 to be moved about the area of the tissue slitting tip 608.

Figure 6C:
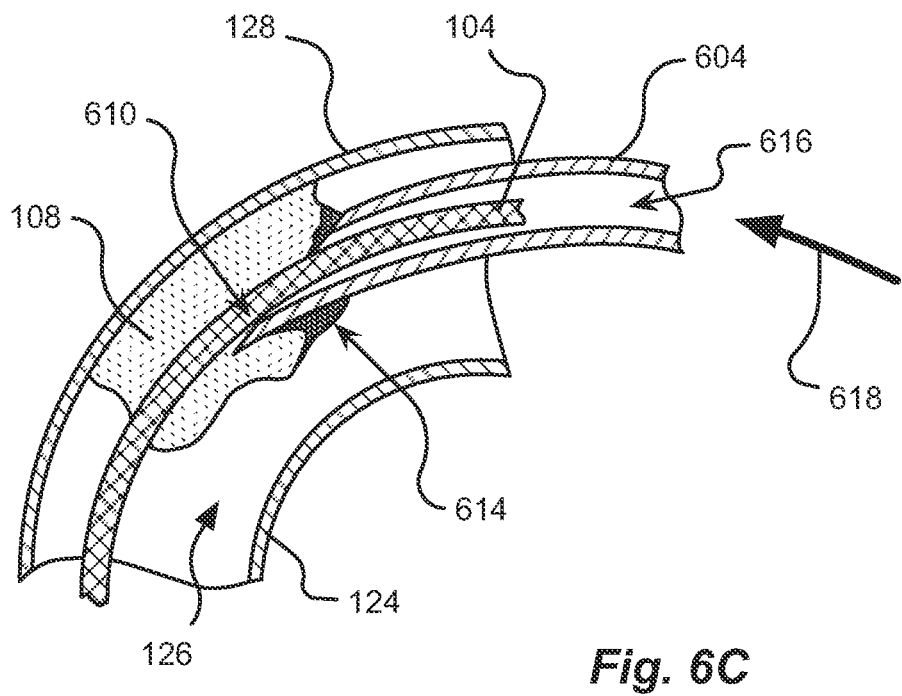
FIG. 6C shows a section view of a curved area of vasculature with a tissue slitting device in a second slitting position in accordance with embodiments of the present disclosure.

FIG. 6C shows a section of a curved area of vasculature with the tissue slitting device 604 in a second slitting position in accordance with embodiments of the present disclosure. As the tissue slitting device 604 is indexed in a direction 618 into the tissue growth 108 the tissue slitting device 604 separates tissue along an axial length of at least one side of the lead 104. In some embodiments, the lead 104 may be subjected to a traction force 120 that may be opposite to the index direction 618 of the tissue slitting device 604. This applied traction force 120 may assist in pulling the lead 104 away from the tissue growth 108 as the lead 104 is separated from containing tissue growth 108.

Figure 6D:
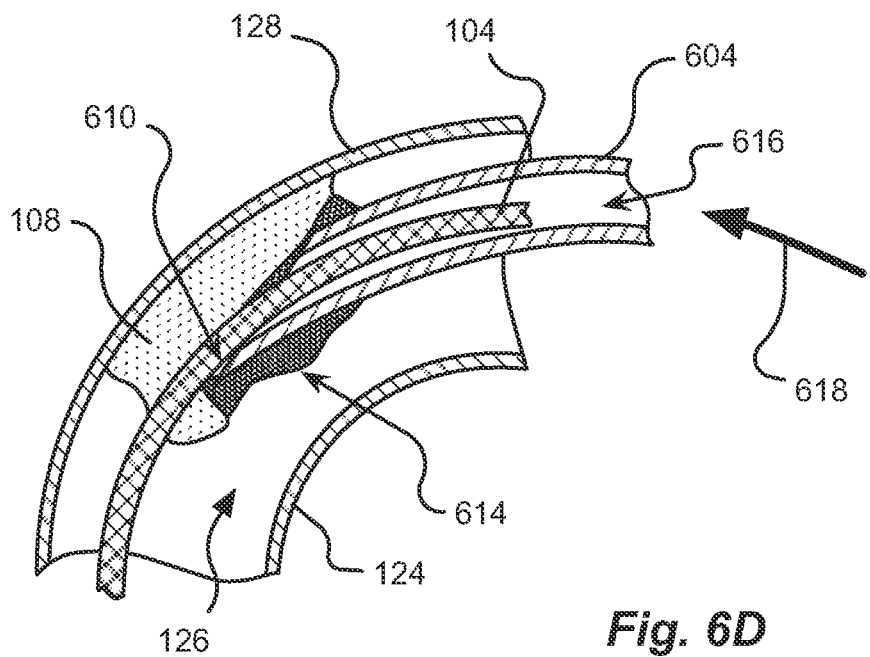
FIG. 6D shows a section view of a curved area of vasculature with a tissue slitting device in a third slitting position in accordance with embodiments of the present disclosure.

FIG. 6D shows a section view of a curved area of vasculature with a tissue slitting device 604 in a third slitting position in accordance with embodiments of the present disclosure. In general, the tissue slitting device 604 is indexed further into the tissue growth 108 such that the tissue growth 108 is almost completely separated from the lead 104 along a length of the tissue growth 108. In some embodiments, slitting at least a portion of the tissue growth 108 may allow the lead 104 to be removed in an explant procedure. For instance, the lead 104 may be subjected to a traction force 120 to pull the lead 104 away from any remaining the tissue growth 108. Additionally or alternatively, the lead 104 may be pulled against the remaining tissue growth 108 that surrounds the lead 104. In other embodiments, the tissue slitting device 604 may be indexed along the entire length of the tissue growth 108 to completely separate the tissue growth 108 from encapsulating, or surrounding, the lead 104.

Figure 7A:
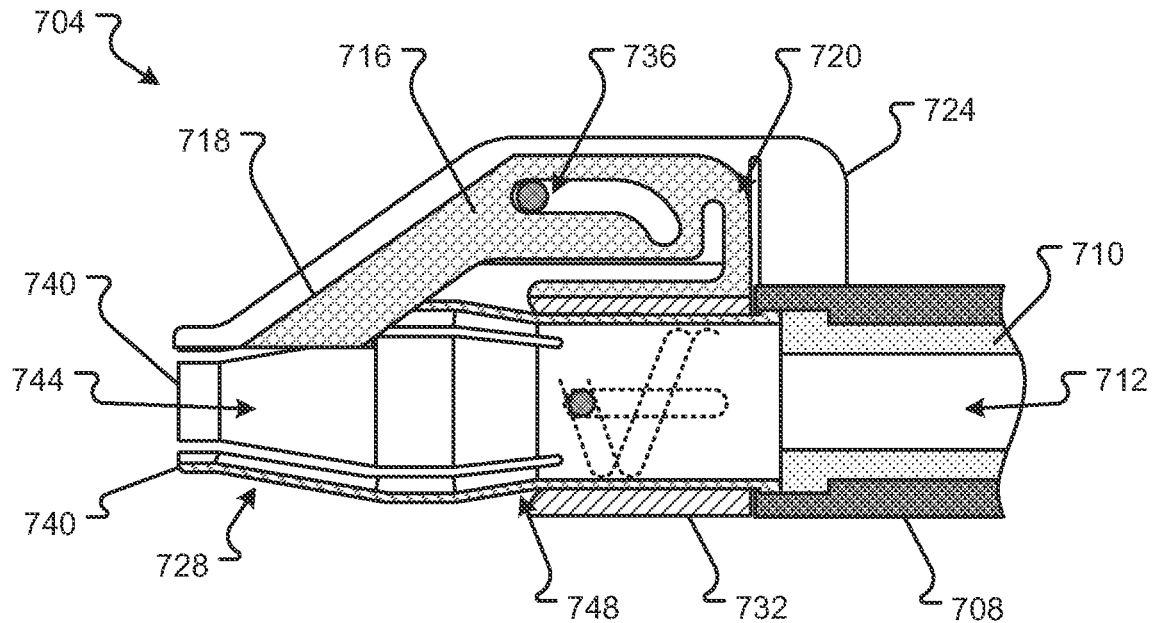
FIG. 7A shows a side view of a tissue slitting apparatus in a first position in accordance with embodiments of the present disclosure.
Figure 7B:
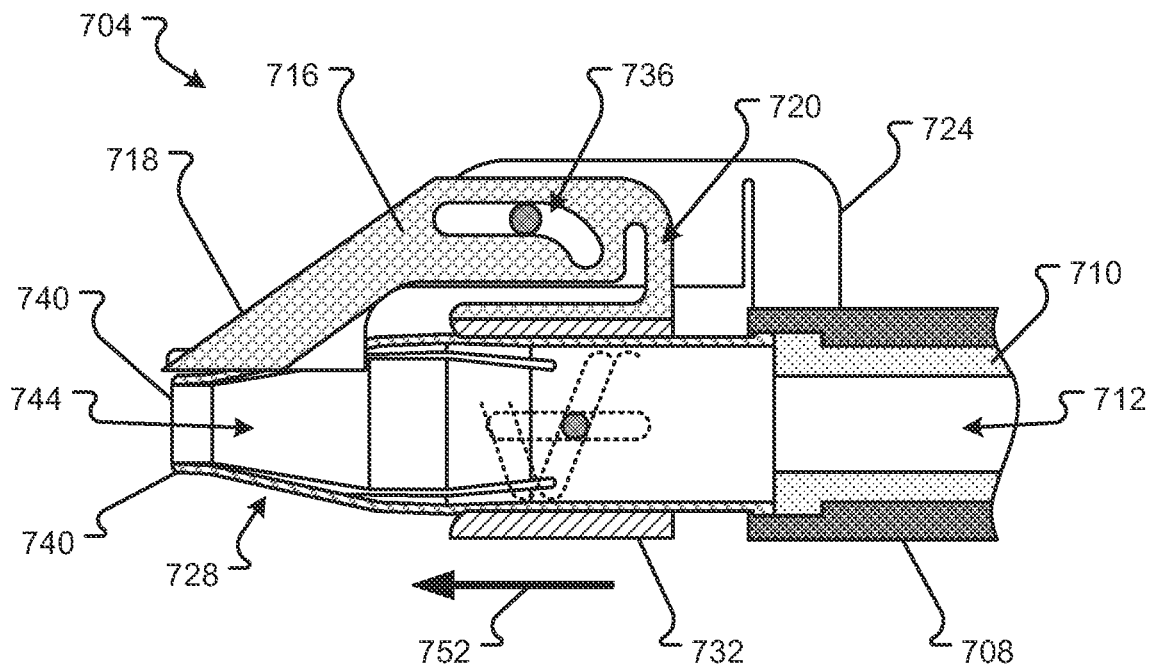
FIG. 7B shows a side view of a tissue slitting apparatus in a second position in accordance with embodiments of the present disclosure.
Figure 7C:
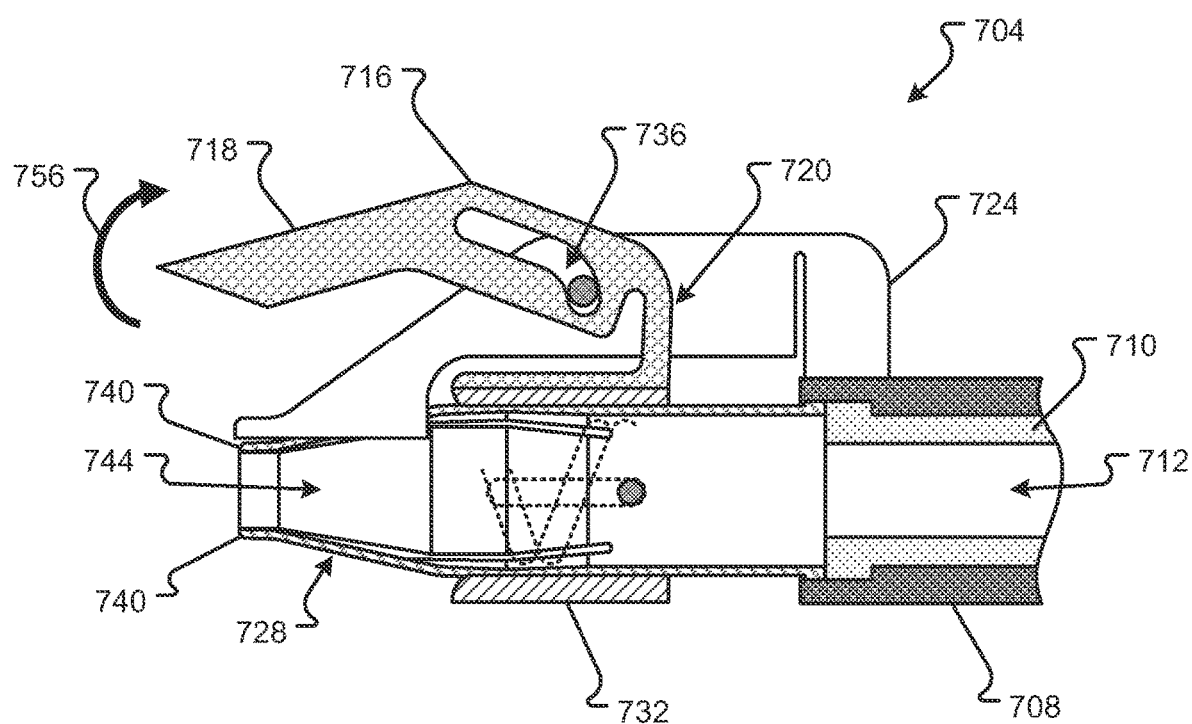
FIG. 7C shows a side view of a tissue slitting apparatus in a third position in accordance with embodiments of the present disclosure.
Figure 8:
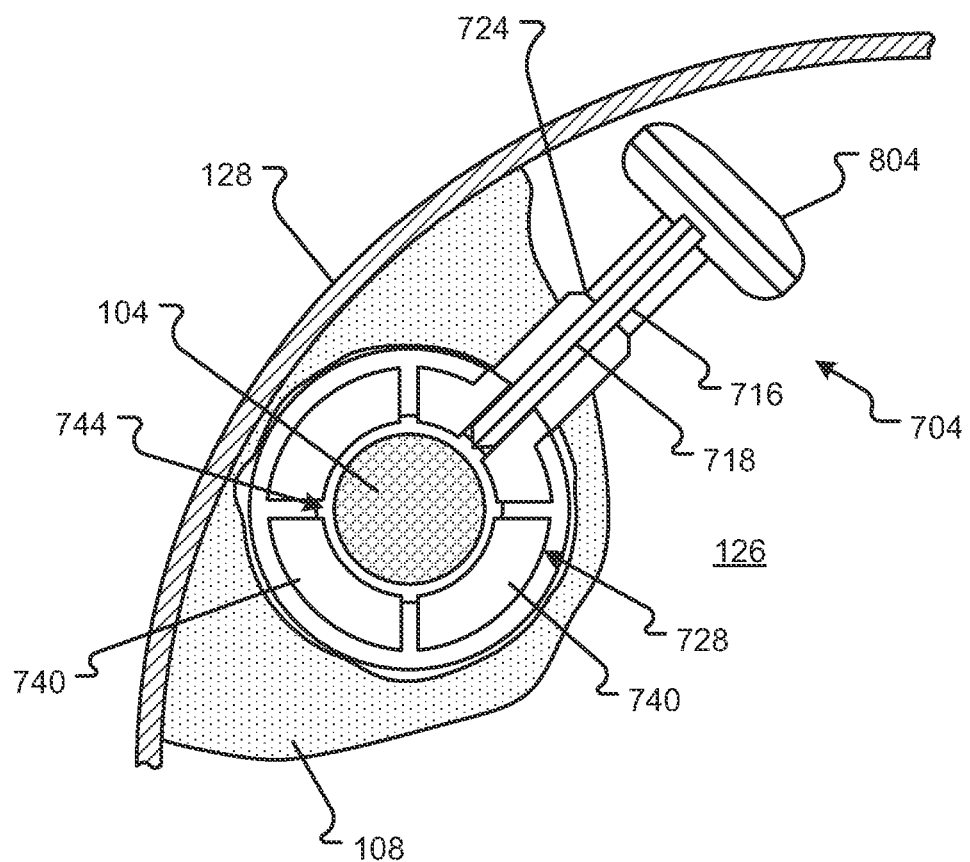
FIG. 8 shows an end view of a tissue slitting device inside an area of vasculature in accordance with embodiments of the present disclosure.
Figure 9:
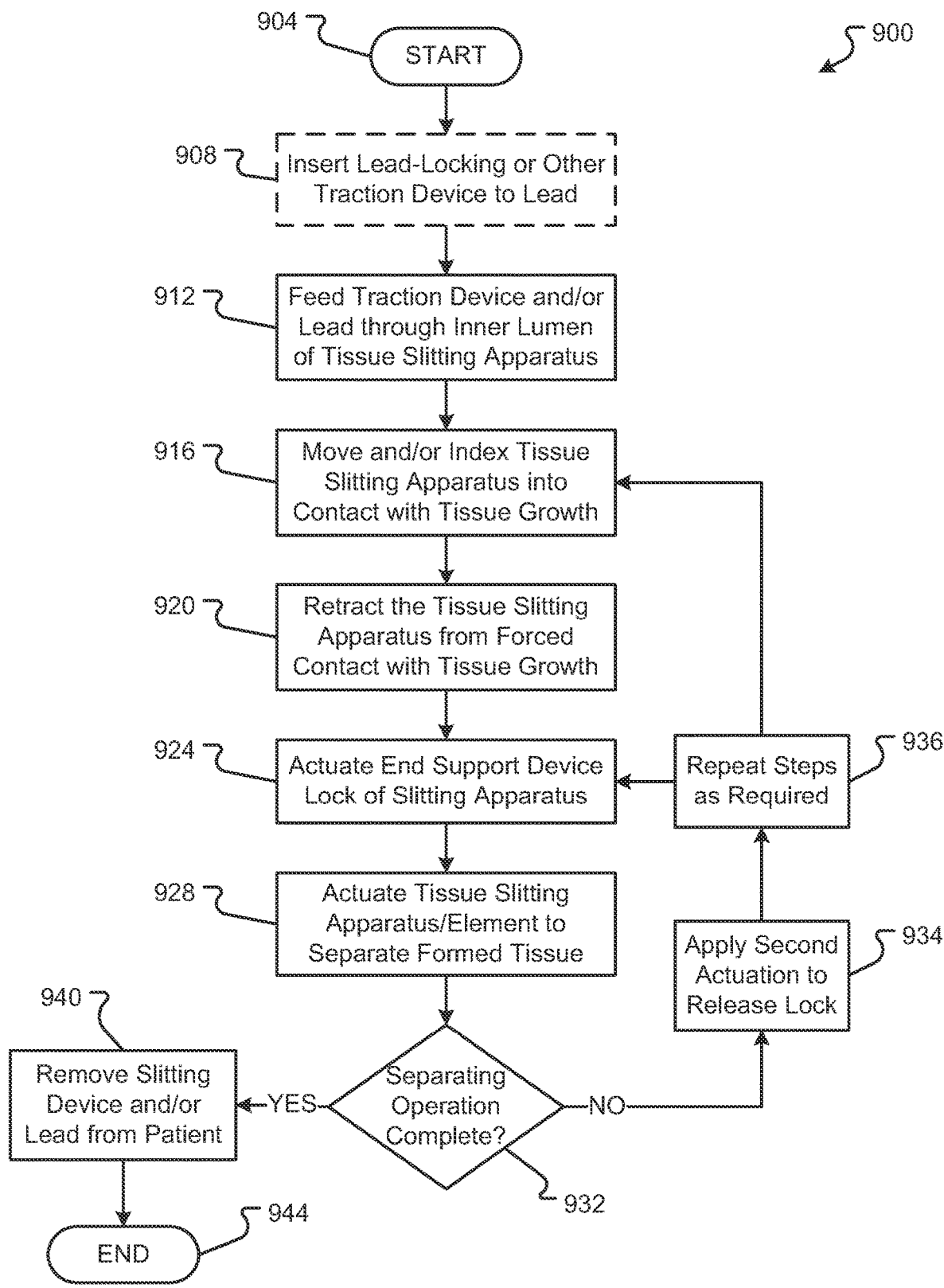
FIG. 9 is a flow diagram depicting a tissue slitting method in accordance with embodiments of the present disclosure.

FIGS. 7-9 are directed to embodiments of a tissue slitting device that include one or more cutting features that are configured to cut at least a portion of a tissue growth 108 along a lead 104 implanted in a patient 102. It should be appreciated that at least one portion of the descriptions accompanying each of the aforementioned figures, namely FIGS. 1-6D, may be used to describe one or more of the features (e.g., methods, systems, tissue slitting devices, components, problems, solutions, arrangements, and the like) associated with the ensuing description. Additionally or alternatively, the ensuing description may apply to one or more features of FIGS. 1-6D.

In any of the embodiments disclosed herein the cutting surface may be guarded by a mechanical sheath. A mechanical sheath may include at least one surface that acts to guard and/or protect a cutting surface from being accidentally exposed to one or more sensitive areas of the vasculature during navigation of a tissue slitting device within a patient 102. In one embodiment, a mechanical sheath may at least partially shroud a portion of a cutting surface with a compliant material (e.g., silicone, polyurethane, rubber, polymer, combinations thereof, and the like). It is anticipated that the compliant material may be compressed when subjected to an operation force. The compression of the compliant material may subsequently expose the cutting surface of the tissue slitting device.

In another embodiment, the mechanical sheath may include a non-compliant material (e.g., metal, carbon fiber, plastic, resin, combinations thereof, and the like) that is configured to at least partially shroud a portion of a cutting surface. The non-compliant material mechanical sheath may be configured to at least partially shroud the cutting surface via a compliant member (e.g., spring, flexure, compliant material, combinations thereof, etc.) in connection with the non-compliant member that maintains a shrouded position of the non-compliant material mechanical sheath. Upon subjecting the non-compliant material mechanical sheath to an operational force, the operational force may be directed to the compliant member, which subsequently exposes the cutting surface from the mechanical sheath.

Referring now to FIG. 7A, a tissue slitting apparatus 704 is shown in a first position in accordance with embodiments of the present disclosure. In some embodiments, the tissue slitting apparatus 704 comprises a flexible shaft 708, an inner lumen 712, at least one slitting element 716 having at least one cutting surface 718, a pivot area 720, a mechanical sheath 724, an end support device 728, an end support device lock 732, and an actuation guide arrangement 736. In some embodiments, the tissue slitting apparatus may include an actuation element 710. The inner lumen 712 can be disposed between the proximal and distal end of the tissue slitting device 704, and may include a lumen of the flexible shaft 708 and/or the end support device 728 (e.g., a collet lumen). In some embodiments, the inner lumen 712 may be configured to allow a lead 104 and/or other objects to pass therethrough (e.g., a lead-locking device, traction device, snare tool, etc.). As can be appreciated, the tissue slitting apparatus 704 may be indexed and/or guided along the lead 104 via the inner lumen 712 of the apparatus 704.

The tissue slitting apparatus 704 may be configured to engage with the tissue growth 108 in a patient 102 at a distal tip of the apparatus 704. In some embodiments, the distal tip of the apparatus 704 may be equipped with a slitting element 716 configured to cut the tissue growth 108. Additionally, the slitting element 716 may be configured to part the tissue as it cuts. As the slitting element 716 is moved into the tissue growth 108, the cutting surface 718 of the slitting element 716 may sever the tissue while simultaneously parting it along at least one side of the cutting surface 718.

In any of the embodiments disclosed herein, disposition of the slitting element 716 of the tissue slitting apparatus 704 may be arranged as one or more shapes, angles, and dimensions. In one embodiment, the slitting element 716 may be arranged at an angle ranging from 10 to 50 degrees from a plane that is coincident with at least two points on an axis running along the lumen 712 of the tissue slitting device 704. As can be appreciated, the slitting element 716 cutting surface 718 of the tissue slitting apparatus 704 may be defined by its axial length from the distal end of the apparatus 704. In one embodiment, the axial length of the cutting surface 718 of the slitting element 716 may range from 0.025" to 1.500". In another embodiment, the axial length of the cutting surface 718 of the slitting element 716 may range from 0.050" to 0.750".

In some embodiments, the end support device 728 may be configured to provide a clamping force to a lead 104 within the vasculature of a patient 102. In one example, the clamping force may be used to grasp the lead 104 and/or provide support for the slitting element 716 disposed adjacent to the end support device 728. Among other things, the end support device 728 can allow the slitting element 716 to slit tissue, while at least some of the forces provided by the slitting element 716 engaging and/or slitting tissue are at least partially supported at the distal end of the tissue slitting apparatus 704. The end support device 728 may be arranged as one or more end support elements 740 that are capable, alone or in combination, of restricting movement of the flexible shaft 708 of the tissue slitting apparatus 704. In some embodiments, the end support device 728 may include a proximal and a distal end. As can be appreciated, the end support device 728 may be attached to the distal end of a flexible shaft 708. In one embodiment, the proximal end of the end support device 728 may be attached to the distal end of the flexible shaft 708.

In some embodiments, the end support device 728 may be arranged as a collet (e.g., a chuck, vise, spring collet, etc.) having a proximal and a distal end, with at least one tapered outer surface 748, and a collet lumen 744 running from the proximal to the distal end of the end support device 728. In one embodiment, the collet lumen 744 may be coincident and/or coaxial with the inner lumen 712 of the apparatus 704. As can be appreciated, the end support device 728 may be separated into two or more end support elements 740 that, when subjected to an actuation force, are configured to reduce an internal diameter of the collet lumen 744. A reduction in dimension of the internal diameter of the collet lumen 744 may cause at least some of the actuation force to be applied as a clamping force around a lead 104 or other implanted object in an area defined by the collet lumen 144. The actuation force may be applied by a directed force transmitted via an end support device lock 732 that is configured to contact the tapered outer surface 748 of the end support device 728. The tapered outer surface 748 of the end support device 728 can direct the actuation force toward the center, and/or collet lumen 744, of the end support device 728. In other words, the end support device 728 may be closed (i.e., reducing the internal diameter of the collet lumen 744) from the end support device lock 732 contacting the tapered outer surface 748 of the end support device 728.

FIG. 7A shows the end support device 728 and end support device lock 732 of a tissue slitting apparatus 704 in an open condition in accordance with embodiments of the present disclosure. In other words, each of the end support elements 740 of the end support device 728 are shown in a first position (i.e., open) with an end support device lock 732 in an open state. As provided above, the end support device 728 may be arranged as a collet (e.g., a chuck, vise, spring collet, etc.) having a proximal and a distal end, with at least one tapered outer surface 748, and a collet lumen 744 running from the proximal to the distal end of the end support device 728. In some embodiments, the collet lumen 744 may be concentric with and/or coincident with an inner lumen 712 of the flexible shaft 708. It is anticipated that the collet lumen 744 may include an internal diameter sized to allow a lead 104 to pass therethrough, where the internal diameter of the collet lumen 744 is greater than an outer diameter of the lead 104 when the collet lumen 744 is in an open state.

Additionally or alternatively, the slitting element 716 may be operatively connected to, and arranged to pivot about, a pivot area 720 to achieve a sweeping and/or arced cutting action of a cutting surface 718 of the slitting element 716. In one embodiment, the sweeping cutting action may be achieved by moving the slitting element 716 about a pivot area 720 having at least one of a pivot point, flexure, flexure area, cantilevered member, four-bar mechanism, compound mechanism, and the like. As can be appreciated, the pivot area 720 may be located distal to or proximal to a cutting surface 718 of the slitting element 716. In some cases, the pivot area 720 of the slitting element 716 may be attached to the end support device 728, the end support device lock 732, and/or the flexible shaft 708 of the tissue slitting apparatus 704. In any event, the slitting element 716 is configured to provide at slit a region of the tissue growth 108 by cutting into the tissue growth 108 while the slitting element 716 is supported by the end support device 728.

It is anticipated that the slitting element 716 may be configured as a blade positioned perpendicular to the outer circumferential surface of the lead 104. The blade, or cutting surface 718, of the slitting element 716 may be configured to move along with the end support device lock 732. In other words, the slitting element 716 may be operatively connected to the end support device 728 and/or the end support device lock 732. For example, the slitting element 716 may be disposed proximal to the distal end of the end support device 728, and as the end support device lock 732 engages the end support device 728, and/or closes an internal diameter of the collet lumen 744, the slitting element 716 may move in a direction toward the distal end of the end support device 728. In some cases, the movement of the slitting element 716 may be a ratio of the movement of the end support device lock 732 (e.g., 4:1, 2:1, 1:1, 1:2, 1:4, 1:16, and/or ranges therebetween). Additionally or alternatively, the slitting element 716 may be configured to move after a movement of the end support device 728 and/or end support device lock 732.

In some embodiments, the slitting element 716 may be caused to contact the lead 104 at a circumferential surface of the lead 104 before the slitting element 716 performs a cutting action. Among other things, contact with the lead 104 may allow the slitting element 716 to cut the tissue growth 108 from a lead surface outwardly toward an open area 126 of the vessel. In other words, the circumferential surface of the lead 104 may act as a cutting reference point for the slitting element 716 to base from, and/or return to, during a progressive cutting operation.

Additionally, the slitting element 716 may be equipped with a wedge to peel the tissue away as it is being cut by the cutting surface 718 of the slitting element 716. Additionally or alternatively, the angle of the cutting surface 718, or blade, relative to the axis, and/or outer circumferential surface, of the lead 104 may be configured to achieve an adequate cutting angle in the tissue growth 108, such that the tissue 108 is slit in a manner to best achieve lead 104 removal. That is, due to the overall size of the lumen 712, a small angle itself may create a sharp leading edge sufficient to cut and slit the tissue growth 108. The angle may also create smooth translation and slitting of the remainder of the tissue as the tissue slitting apparatus 704 traverses longitudinally along a direction of the lead 104.

FIG. 7B shows a side view of a tissue slitting apparatus in a second position in accordance with embodiments of the present disclosure. For example, the tissue slitting device 704, or apparatus, may be presented adjacent to a tissue growth 108 along a lead 104. The tissue slitting apparatus 704 may anchor to the lead 104 via an actuation of the end support device 728. Once anchored, or as the apparatus is being anchored, the slitting element 716 may move toward, and even engage, a tissue growth 108. The movement of the slitting element 716 may be caused by one or more of a pin and groove, cam profile, wedge, expanding member, and the like. For example, an end support device lock 732 may be moved in a first direction 752, which can engender an actuation of an end support device 728 and a corresponding movement of a slitting element 716. In part, the movement of the slitting element 716 may be achieved by the slitting element 716 being operatively connected to the end support device 728 and/or the end support device lock 732. The movement of the slitting element 716 in the first direction 752 may expose a cutting surface 718 of the slitting element 716 from a mechanical sheath 724. As can be appreciated, such movements may be controlled as to speed, acceleration, distance, angle, dwell, return action, relative movement, etc. In one example, the end support device 728 may be caused to close upon, and apply at least one clamping force to, a lead 104 after which the slitting element 716 may move. This movement can be achieved in a cam arrangement by providing a dwell for the slitting element 716 at a first section of the cam profile. It is anticipated that various combinations and movements relative to the end support device 728 may be used to achieve a distal end supported slitting action via the slitting element 716.

FIG. 7B shows the end support device 728 and end support device lock 732 of a tissue slitting apparatus 704 in a closed condition in accordance with embodiments of the present disclosure. In some embodiments, the end support device lock 732 may be actuated via an actuation element 710 to move in a first direction 752 toward the distal end of the apparatus 704. As the end support device lock 732 is subjected to the actuation force the internal diameter of the collet lumen 744 may be reduced. For example, each of the one or more end support elements 740 may be moved toward the collet lumen as shown in FIG. 7B. A reduction in dimension of the internal diameter of the collet lumen 744 may cause at least some of the actuation force to be applied as a clamping force around a lead 104 or other implanted object in an area defined by the collet lumen 744. This force may anchor the distal end of the tissue slitting apparatus 704 to the lead 104. As disclosed herein, the actuation force may be applied by a directed force transmitted via an actuation element 710 to an end support device lock 732 that may be configured to contact the tapered outer surface 748 of the end support device 728. The tapered outer surface 748 of the end support device 728 can direct the actuation force toward the center of the collet lumen 744. In other words, the end support device 728 may be closed (e.g., by reducing the internal diameter of the collet lumen 744) from the end support device lock 732 contacting the tapered outer surface 748 of the end support device 728.

FIG. 7C shows a side view of a tissue slitting apparatus 704 in a third position in accordance with embodiments of the present disclosure. As shown, the tissue slitting element 716 being moved toward the distal end of the apparatus 704 (e.g., in the first direction 752 described in conjunction with FIG. 7B) may continue to move to a further distal position (e.g., further into a tissue growth 108) and/or provide an arced, or lifted, cutting action (e.g., over a section of the engaged tissue growth 108) shown by lift direction 756. Additionally or alternatively, the slitting element 716 may wedge into an area between the lead 104 and a tissue growth 108 as it moves toward a tissue growth 108, and cut in an arced, or lifted, motion in lift direction 756, away from the lead 104 toward an outside region of a tissue growth 126. This sweeping motion, shown by lift direction 756, can allow the slitting element 716 to first contact tissue at least partially surrounding a lead 104 in an area where the tissue growth 108, and the tissue fibers, may be placed under tension. The tension of the fibers may be caused by the slitting element 716 as it stretches the fibers away from the lead 104 during its movement when in contact with the tissue. Among other things, the tension placed on the tissue growth 108 fibers can provide a taught area for the cutting surface 718 of the slitting element 716 to engage and cut along. In some embodiments, the slitting element 716 may return to a first position (e.g., in contact with the lead 104, adjacent to the lead 104, and/or in a neutral position, etc.)

after a cutting action has been made. This action may be achieved via the one or more movement elements (e.g., the actuation element 710, end support device 728, end support device lock 732, actuation guide arrangement 736, etc., and combinations thereof) as disclosed herein.

Additionally, embodiments of the tissue slitting apparatus disclosed herein may include at least one fluorescing material or marker (e.g., radiopaque band, marker, and the like). In some embodiments, the radiopaque marker may be arranged about and/or adjacent to a slitting element of the tissue slitting apparatus. The radiopaque marker, may assist in identifying a location of the slitting element 716 via a monitoring device. Examples of radiopaque markers may include, but are in no way limited to, materials and/or particles containing tantalum, tungsten, carbide, iridium, bismuth oxide, barium sulfate, cobalt, platinum and/or alloys and combinations thereof. In some embodiments, the inner lumen 712 may be configured to allow a lead 104 and/or other objects to pass therethrough (e.g., a lead-locking device, traction device, snare tool, etc). As can be appreciated, the tissue slitting apparatus 704 may be indexed and/or guided along the lead 104 via the inner lumen of the apparatus 704.

FIG. 8 shows an end view of a tissue slitting apparatus 704 inside an area of vasculature in accordance with embodiments of the present disclosure. In some embodiments, a slitting element 716 is oriented at least partially within the vasculature of a patient 102, which may allow the apparatus 704 to be routed through the vasculature without presenting sharp edges, cutting surfaces 718, or slitting elements 716 toward sensitive areas. The slitting element 716 oriented within the vasculature may allow the cutting surface 718 of slitting element 716 to be biased away from the vessel wall of a patient's vasculature. In other words, the tissue slitting element 716 may be oriented toward the tissue growth 108 in connection with the lead 104. A slitting orientation control feature 804 may be operatively attached to the tissue slitting apparatus 704 at, or adjacent to, the distal end of the apparatus 704. The slitting orientation control feature 804 may act to safely orient the slitting element 716 within a patient 102. In one embodiment, the slitting orientation control feature 804 may be connected to the mechanical sheath 724. It is anticipated that the slitting orientation control feature 804 may be arranged in a known relation to a slitting element 716. For instance, the slitting element 716 may be positioned at a dimension from a vessel wall contact edge or surface of the slitting orientation control feature 804, such that the dimension prevents the slitting element 716 from contacting a vessel wall 124, 128. As can be appreciated, the slitting orientation control feature 804 may prevent full 360 degree rotation of the tissue slitting apparatus 704 within a section of the vasculature of a patient 102. In one example, a tissue slitting apparatus 704 may be directed inside a patient 102 toward a tissue growth 108. As the apparatus 704 engages the tissue growth 108, any unwanted, or dangerous, rotation of the apparatus 704 that may present the slitting element 716 to a vessel wall 124, 128 can be prevented by the slitting orientation control feature 804 first contacting the vessel wall 124, 128. Such contact can prevent further rotation of the apparatus 704 and the slitting element 716 in a direction toward the vessel wall 124, 128 in contact with the slitting orientation control feature 804. Additionally or alternatively, the apparatus 704 may be allowed to rotate away from the vessel wall 124, 128 such that the slitting orientation control feature 804 moves toward the open area 126 (and safe section) of the vessel.

In accordance with embodiments of the present disclosure, the slitting element 716 may be advanced into the tissue growth 108. This advancement may be continuous or periodic. Additionally or alternatively, the slitting element 716 may be actuated in a direction toward and away from the tissue such that the slitting element 716 is presented to an area of the tissue growth 108, removed from the area, and re-presented to an area of the tissue growth 108 to successively cut the tissue growth 108 over a number of movements. For example, the tissue growth 108 can be cut in a similar manner to that of an axe chopping at a tree or of scissors cutting material. In any embodiment disclosed herein, fraction force may be applied to the lead 104 during the cutting of the tissue growth 108. Among other things, traction force 120 can prevent tears, punctures, and/or other catastrophic failures caused by the force exerted on the tissue growth 108 and/or adjacent vasculature by the tissue slitting apparatus 704.

It is anticipated that the slitting element 716 may be manufactured from a material with a suitable hardness for slitting tissue. In some embodiments, the slitting element 716 may be manufactured from a polymeric material with a durometer configured to cut a patient's tissue. Examples of polymeric material may include, but are not limited to, plastics, silicone, polytetrafluoroethylene ("PTFE"), polyethylene, polyurethane, polycarbonate, polypropylene, polyvinyl chloride ("PVC"), polystyrene, acetal, polyacetal, acetal resin, polyformaldehyde, and the like. In one embodiment, the slitting element 716 may be constructed from a crystalline or amorphous metal alloy. The slitting element 716 may comprise at least a portion of the distal tip of the tissue slitting apparatus 704. As can be appreciated, the slitting element 716 may comprise a metal insert. Examples of slitting element 716 metals may include, but are not limited to, steel, stainless steel (e.g., austenitic type 304, 316, martensitic type 420, 17-4, etc.), aluminum, titanium, tungsten carbide, silver, platinum, copper, and combinations thereof. In one embodiment, the metal may be hardened to, among other things, maintain a sharp edge during the tissue slitting process.

Additionally or alternatively, the slitting element 716 or cutting surface 718 may be removably attached to the distal tip of the tissue slitting apparatus 704. Benefits of a removably attached slitting element 716 allow for quick replacement of cutting surfaces 718 during lead removal procedures. As can be appreciated, the replacement of the cutting surface 718 may be initiated upon detecting that the cutting surface 718 of the slitting element 716 is dulling. In some cases the cutting surface 718 may be replaced with a different style of blade. The style of blade may be configured to suit a number of desires, including but not limited to, navigating difficult areas in a patient (e.g., using a curved blade, etc.), cutting difficult, dense, and/or hard tissue (e.g., using a serrated blade, a hardened blade, and combinations thereof, etc.), cutting tissue in confined and/or low-growth areas (e.g., using a miniature blade), and even removing the blade completely (e.g., using the tissue slitting device as a counter-traction sheath, etc.).

In some embodiments, the tissue slitting apparatus 704 disclosed herein may include at least one non-traumatic leading edge disposed at the most distal end of the apparatus 704. The non-traumatic leading edge may include a distal end and a proximal end. Non-traumatic surfaces on the leading edge of the device may include but are not limited to, spheroidal, ball-nose, radiused, smooth, round, and/or other shapes having a reduced number of sharp edges. These non-traumatic surfaces may be configured to prevent accidental puncture or harmful contact with the patient 102. The non-traumatic leading edge may be configured to include a tapered and/or a wedge-shaped portion. In some cases the cross-sectional area of the tapered portion increases along a length of the non-traumatic leading edge from the distal end to the proximal end of the leading edge. A knife-edge and/or cutting surface 718 may be disposed proximal to the non-traumatic leading edge of the tissue slitting apparatus 704.

The non-traumatic leading edge may be positioned to insert into an area between the tissue growth 108 and the implanted lead 104. In some cases the tapered geometry and the arrangement of the tissue slitting apparatus 704 tip may allow the most distal portion of the non-traumatic leading edge to bias against the lead 104 and wedge under any surrounding tissue growth 108. As the non-traumatic leading edge is indexed further into the tissue growth 108, the tissue growth 108 is caused to stretch and pull away from the lead 104. Once the non-traumatic leading edge is engaged with the tissue growth 108, the cutting surface 718 of the tissue slitting apparatus 704 may be caused to slit the tissue along a length of the tissue growth 108. As can be appreciated, the slitting element 716 may include, but is not limited to, one or more cutting surfaces 718 and tissue slitting apparatus 704 disclosed herein.

Referring to FIG. 9, a tissue slitting method 900 will be described in accordance with at least some embodiments of the present disclosure. The method 900 begins at step 904 and proceeds by optionally connecting a lead-locking device or other traction device to a lead 104 (step 908). In some embodiments, the lead-locking device may be inserted into the core of an implanted lead 104. In other embodiments, a traction device may be connected to the lead 104 to provide traction on the lead 104. For instance, mechanical traction can be achieved in leads 104 by inserting a locking stylet into the lead 104 and applying a pull force onto the lead 104 via the locking stylet.

Once a traction device is attached to the lead 104, the method 900 continues by feeding the fraction device and/or the lead 104 through the internal, or inner, lumen 712 of the tissue slitting apparatus 704 (step 912). In some embodiments, a lead-locking device may be optionally used. In one embodiment, the lead 104 itself may be threaded through the inner lumen 712 of the tissue slitting apparatus 704. In any event, the lead 104 and/or the lead-locking device may be threaded through a lumen 712 associated with the tissue slitting apparatus 704. For example, the lead-locking device may be inserted through the lumen in an implanted lead 104 and attached to the internal portions of the implanted lead 104, which can be at the distal portion or proximal to the distal portion of the lead 104. The tissue slitting apparatus 704 may be part of a catheter that rides over the external portion of the lead 104 and lead-locking device and is configured to remove tissue along an axial length of the tissue 108 in contact with the lead 104.

As the tissue slitting apparatus 704 is engaged with the lead 104, a slight fraction force may be applied to the lead 104 to allow the tissue slitting apparatus 704 to guide along the lead 104. The tissue slitting apparatus 704 can be moved toward the first formed tissue growth 108 while applying a mechanical fraction force to the lead 104 itself, through a locking stylet, and/or other traction device. Mechanical traction force may be applied with appropriate force to prevent tearing the vein or artery (e.g., vessel) wall by moving the lead 104 and tissue before they are separated. In some embodiments, the tissue slitting apparatus 704 may be observed moving inside a patient 102 via a fluoroscope or other monitor. It is anticipated that the distal tip, or some other area, of the tissue slitting apparatus 704 may include a fluorescing material or marker (e.g., radiopaque band, etc., and the like as previously described). This fluorescing material or marker may be used to aid in monitoring the movement of the tissue slitting apparatus 704 when it is inside a patient 102.

Next, the method 900 continues by moving the tissue slitting apparatus 704 into contact with the formed tissue growth 108 (step 916). For example, the tissue slitting apparatus 704 may be advanced until resistance of movement along the lead 104 is detected. In one embodiment, the location of the tissue slitting apparatus may be determined using one or more imaging modality (e.g., IVUS, OCT, 3D, and others as disclosed herein, etc.). In some embodiments, the slitting element 716 of the tissue slitting apparatus 704 may be oriented toward the center of the vessel, or away from the vessel wall 124, 128 connecting the lead 104 to the vessel. In addition to preventing accidental puncture, trauma, or other damage to the delicate surfaces of the vasculature this orientation of the tissue slitting apparatus 704 may aid in the slitting and peeling away of the tissue 108 from the implanted lead 104. While applying mechanical traction force, the leading portion (of the tissue slitting apparatus 704) may include a slitting element 716 having a sharp cutting surface 718, which may be configured to cut into the tissue growth 108. As the tissue slitting apparatus 704 traverses along the lead 104, the slitting element 716 of the tissue slitting apparatus 704 may be configured to continue to separate the formed tissue 108. Additionally the slitting element 716, which may include an angle and/or tapered portion, can act to cause a stretching of the formed tissue growth 108 at the point where it engages with the tissue slitting element 716. This stretching of tissue may assist in the slitting operation by causing tension on the fibers of the tissue growth 108 that, when slit, pull back (or away) from the tissue slitting apparatus 704 engagement area.

The method 900 continues by retracting the tissue slitting apparatus 704 from a forced contact with the tissue growth 108 (step 920). In some embodiments, refracting the tissue slitting apparatus 704 may include using the imaging modality to position the tissue slitting apparatus 704 relative to the tissue growth 108. For example, once the tissue slitting apparatus 704 meets a tissue growth 108, the apparatus 704 may be slightly refracted from intimate contact with the tissue growth 108. In one embodiment, a retraction of the tissue slitting apparatus 704 may not be required to perform the method 900 provided herein.

Next, the method 900 continues by actuating the end support device lock 732, such that the end support device 728 locks onto the lead 104 (step 924). In some embodiments, locking the end support device 728 may prevent further movement of the tissue slitting apparatus 704 along the lead 104. Additionally or alternatively, the end support device lock 732 can provide support for the slitting element 716 at the distal end of the tissue slitting apparatus 704. In one embodiment, the end support device lock 732 may be actuated via a mechanical force applied from an actuation element 710. The mechanical force may be at least one of a linear translation, rotational translation, electromotive force, cam movement, and the like. As can be appreciated, the actuation force may be applied to the actuation element 710 such that the actuation force translates into a movement of the end support device lock 732. In some embodiments, the end support device lock 732 may move along an actuation guide track and/or a tapered outer surface 748 of the end support device 728. This move along the tapered outer surface 748 of the end support device 728 may cause one or more end support elements 740 to close, or reduce a collet lumen 744 diameter, such that the end support device 728 locks onto the lead 104.

The method 900 continues by actuating the slitting element 716 of the tissue slitting apparatus 704 (step 928). As the slitting element 716 is actuated, the cutting surface 718 of the slitting element 716 may be exposed from a sheathed position. For instance, the actuation of the slitting element 716 may move the cutting surface 718 from a position within the mechanical sheath 724 of the tissue slitting apparatus 704. One example of an actuation element 710 may include a shaft operatively connected to the slitting element 716. In this example, an actuation force may be applied to the actuation element 710 such that the actuation force translates into a movement of the slitting element 716. The actuation force can be at least one of a linear translation, rotational translation, electromotive force, cam movement, and the like.

Additionally or alternatively, the movement of the slitting element 716 may include one or more paths. For instance, a cam profile (e.g., a groove and pin, a cam surface and a cam follower, etc.) may be employed such that the slitting element 716 can make one or more of linear, arced, sweeping, lifting, and other movements. In some embodiments, the actuation of the slitting element 716 and the end support device lock 732 may be performed by a single actuator and/or actuation force.

In any event, it is anticipated that the slitting element 716 may introduce a cutting surface 718 to the tissue growth 108 at a point where the tissue growth 108 meets a lead 104, or other implanted object. As the cutting surface 718 moves into the tissue the slitting element 716 may lift in a direction away from the lead 104. This movement can cause the cutting surface 718 to cut the tissue. In some embodiments, and because the end support device 728 has locked onto the lead 104 at the distal end of the tissue slitting apparatus 704, the slitting element 716 may make sequential and/or sweeping cuts into the tissue growth 108 to create the slit as described herein. Among other things, the lifting motion of the slitting element 716 and cutting surface 718 can place the fibers of the tissue growth 108 under tension while the cutting surface 718 cuts the tissue of the tissue growth 108. As can be appreciated, supporting the slitting element 716 via locking the end support device 728 can allow for greater cutting forces to be applied via the slitting element 716. Once the slitting element 716 has performed the cutting operation, the slitting element 716 may return to its original position such that the cutting surface 718 is sheathed.

The method 900 continues when the tissue slitting apparatus 704 has completed the cutting operation (step 932). At this point, the end support device lock 732 may be unlocked (step 934). For instance, the steps of actuating the end support device lock 732, as described above, may be performed in reverse. In one embodiment, the end support device lock 732 may be actuated via a mechanical force applied from an actuation element 710. In some embodiments, the end support device lock 732 may move along an actuation guide track and/or a tapered outer surface 748 of the end support device 728 in a direction that may cause one or more end support elements 740 to open, or increase a collet lumen 744 diameter, such that the end support device 728 is released from a locked position. This unlocked end support device 728 can allow the tissue slitting apparatus 704 to move along the lead 104.

In the event that the tissue growth 108 is still restricting a movement of the lead 104, the steps above may be repeated with the tissue growth 108 or other tissue growths found along the length of the lead 104 (step 936). Once the lead 104 has been released from the restrictive forces of tissue growth, the method 900 may continue by removing the lead 104 through the inner lumen 712 of the tissue slitting apparatus 704 (step 940). The method ends at step 944.

In some embodiments, the tissue slitting apparatus 704 may be indexed forward (into the tissue formation 108) continuously or periodically. In other embodiments, the tissue slitting apparatus 704 may be repeatedly indexed into and removed from the engagement area of the formed tissue growth 108. It is anticipated that each time the tissue slitting apparatus 704 is indexed into the engagement area the device 704 can make a successively longer slit in the formed tissue growth 108. Actuation may be achieved via an actuator that is operatively connected to the actuation element 710. The actuator may be an electrical motor that is located at the proximal end of the flexible shaft 708. In some embodiments, the actuator may be manually operated via a mechanical movement at the proximal end of the flexible shaft 708 through the actuation element 710 connected to the slitting element 716. In any event, energy from the actuator may be transferred to at least one of the end support device lock 732, end support device 728, and the slitting element 716 via one or more of a shaft, rod, cam, bar, pin, link, groove, combinations thereof, and the like that are configured to transmit force from the proximal end of the tissue slitting apparatus 704 to the at least one of the end support device lock 732, end support device 728, and the slitting element 716.

As described above, the method may be continued by determining whether other tissue growths exist, and if so, indexing the tissue slitting apparatus 704 through each formed tissue growth 108 that is surrounding a section of the implanted lead 104 in the vasculature. Once all of the formed tissue growths 108 are slit, or separated, the tissue slitting apparatus 704 may be removed from the patient 102. Additionally or alternatively, once the slits have been made the lead 104 may be removed by applying a pull force to the lead-locking device in the same direction as the mechanical traction force previously applied to the lead 104. It is anticipated that any movement of the tissue slitting apparatus 704 may be accompanied by an applied mechanical traction force to the lead/lead-locking device.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

Presented herein are embodiments of a tissue separating device, system, and method. As described herein, the device(s) may be electrical, mechanical, electro-mechanical, and/or combinations thereof.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others. By way of illustration, any methodology or modality of cutting tissue may be employed as described herein to effect lead removal from an encased tissue growth.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Summary, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A tissue slitting device comprising:
    a shaft having a distal end, a longitudinal axis, and an inner lumen extending substantially through the shaft;
    an actuation guide comprising a track, wherein the track comprises a linear portion substantially parallel to the longitudinal axis of the shaft and a non-linear portion proximal to the linear portion;
    a cutting edge at the distal end of the shaft, wherein the cutting edge pivots on a pin that follows the track of the actuation guide; and
    a support element having a tapered outer surface and a lumen running therethrough, wherein the lumen of the support element is in communication with the inner lumen of the shaft.

2. The tissue slitting device of claim 1 wherein the cutting edge pivots away from the longitudinal axis of the shaft as the pin travels through the non-linear portion of the guide track.

3. The tissue slitting device of claim 1 wherein the cutting edge pivots away from the longitudinal axis of the shaft as the pin travels through the non-linear portion of the guide track.

4. The tissue slitting device of claim 1 further comprising a tissue slitting element comprising the cutting edge and a slitting orientation control feature disposed adjacent to the distal end of the tissue slitting device, wherein the slitting orientation control feature is configured to prevent rotation of the tissue slitting element into a vessel wall of a patient.

5. The tissue slitting device of claim 1 further comprising an actuation element and an end support device lock operatively connected to the actuation element that moves the end support device lock along the tapered outer surface of the support element and the movement of the end support device lock along the tapered outer surface of the support element reduces a diameter of the lumen running through the support element to provide a clamping force onto an object that is implanted in a patient.

6. The tissue slitting device of claim 1 wherein the support element is arranged as a collet separated into two or more end support elements that, when subjected to an actuation force, reduce an internal diameter of the lumen running through the support element.

7. The tissue slitting device of claim 1 wherein the cutting edge pivots away from a lead implanted in a patient with a lifting motion that produces tension on fibers of a tissue growth around the lead.

8. A tissue slitting device for removing an object implanted in a patient, the tissue slitting device comprising:
    a shaft for insertion into a lumen of the patient, the shaft having a distal end, a longitudinal axis, and an inner lumen extending substantially through the shaft;
    an actuation guide comprising a track, wherein the track comprises a linear portion substantially parallel to the longitudinal axis of the shaft and a non-linear portion proximal to the linear portion;
    a cutting edge at the distal end of the shaft comprising a pin, wherein the cutting edge pivots away from the longitudinal axis of the shaft as the pin travels through the non-linear portion of the guide track; and
    a support element having a tapered outer surface and a lumen running therethrough, wherein the lumen of the support element is in communication with the inner lumen of the shaft.

9. The tissue slitting device of claim 8 further comprising a tissue slitting element comprising the cutting edge and a slitting orientation control feature disposed adjacent to the distal end of the tissue slitting device, wherein the slitting orientation control feature is configured to prevent rotation of the tissue slitting element into a vessel wall of a patient.

10. The tissue slitting device of claim 9 further comprising an actuation element and an end support device lock operatively coupled to the actuation element.

11. The tissue slitting apparatus of claim 10, wherein the actuation element moves the end support device lock along the tapered outer surface of the support element, and wherein the movement of the end support device lock along the tapered outer surface of the support element reduces a diameter of the inner lumen to provide a clamping force onto the object implanted in the patient.

12. The tissue slitting apparatus of claim 8 wherein the support element is arranged as a collet separated into two or more end support elements that, when subjected to an actuation force, reduce an internal diameter of the lumen running through the support element.

13. The tissue slitting apparatus of claim 8 wherein the cutting edge pivots away from the object implanted in the patient with a lifting motion that produces tension on fibers of a tissue growth around the object.

* * * * *